(12) United States Patent
Ogawa et al.

(10) Patent No.: US 8,877,915 B2
(45) Date of Patent: Nov. 4, 2014

(54) TRANSCRIPTION REGULATORY FACTORS FOR MANNANASES OR CELLULASES, AND GENES FOR THE TRANSCRIPTION REGULATORY FACTOR

(75) Inventors: Masahiro Ogawa, Noda (JP); Yasuji Koyama, Noda (JP); Masayuki Machida, Tsukuba (JP)

(73) Assignees: National Institute of Advanced Industrial Science and Technology, Tsukuba-Shi Ibaraki (JP); Noda Institute for Scientific Research, Chiba (JP)

( * ) Notice: Subject to any disclaimer, the term of this patent is extended or adjusted under 35 U.S.C. 154(b) by 226 days.

(21) Appl. No.: 13/202,279

(22) PCT Filed: Mar. 2, 2010

(86) PCT No.: PCT/JP2010/053283
§ 371 (c)(1),
(2), (4) Date: Oct. 28, 2011

(87) PCT Pub. No.: WO2010/101129
PCT Pub. Date: Sep. 10, 2010

(65) Prior Publication Data
US 2012/0142051 A1    Jun. 7, 2012

(30) Foreign Application Priority Data

Mar. 4, 2009    (JP) .................................. 2009-051323

(51) Int. Cl.
C07K 14/38 (2006.01)
C12N 9/44 (2006.01)
C07H 21/04 (2006.01)
A23J 1/18 (2006.01)
C12N 9/42 (2006.01)

(52) U.S. Cl.
CPC .............. C12N 9/2434 (2013.01); C07K 14/38 (2013.01); C12N 9/2451 (2013.01)
USPC ..... 536/23.74; 530/371; 435/200; 435/252.3; 435/252.31; 435/254.11; 435/254.2; 435/254.21; 435/254.3; 435/69.1; 435/325

(58) Field of Classification Search
None
See application file for complete search history.

(56) References Cited

U.S. PATENT DOCUMENTS

| 5,795,764 | A | 8/1998 | Christgau et al. | |
| 6,011,147 | A * | 1/2000 | Nakari et al. | 536/24.1 |
| 2001/0014659 | A1 * | 8/2001 | Convents et al. | 510/392 |
| 2003/0203466 | A1 * | 10/2003 | Kauppinen et al. | 435/200 |
| 2004/0082053 | A1 | 4/2004 | Machida et al. | |
| 2010/0189706 | A1 * | 7/2010 | Chang et al. | 424/94.4 |
| 2011/0016545 | A1 * | 1/2011 | Gray et al. | 800/15 |

FOREIGN PATENT DOCUMENTS

| JP | 2001145485 | 5/2001 |
| JP | 2003164286 | 6/2003 |
| JP | 2005176602 | 7/2005 |

OTHER PUBLICATIONS

Score Report SEQ ID No. 2 downloaded Dec. 2, 2013.*
Score Report SEQ ID No. 1 downloaded Dec. 2, 2013.*
International Search Report (Japanese Patent Office) of International Application No. PCT/JP2010/053283, mailed May 18, 2010.
Fedorova, N. D. et al., "Genomic Islands in the Pathogenic Filamentous Fungus *Aspergillus fumigatus*", PLoS Genetics Apr. 2008, vol. 4:4, pp. 1-13.
Takii, Y. et al., "Comprehensive analysis on *aspergillus oryzae* genes participating in hydrolytic enzymes that specifically express on wheat bran", The Iijima Memorial Foundation for the Promotion of Food Science and Technology, Heisei 17 Nendo Nenpo, 2007, pp. 273-279.
Ogawa, M. et al., "Kojikin Mannanase Tensha Seigyo Inshi ManR no Screening to Kino Kaiseki", Japan Society for Bioscience, Biotechnology, and Agrochemistry 2009 Nendo (Heisei 21 Nendo) Taikai Koen Yoshishu, Mar. 2009, p. 284.
Stalbrand, H. et al., "Cloning and Expression in *Saccharomyces cerevisiae* of a *Trichoderma reesei* β-Mannanase Gene Containing a Cellulose Binding Domain", Applied and Environmental Microbiology, Mar. 1995, vol. 61:3 pp. 1090-1097.
Tang, C.M., et al., "The cel4 Gene of Agaticus Encodes a β-Mannanase ", Applied and Environmental Microbiology, May 2001, vol. 67:5, pp. 2298-2303.
Mendoza, N.S., et al., "Cloning and Sequencing of β-mannanase gene from *Bacillus subtilis* NM-39", Biochimica et Biophysica Acta 1243 (1995), pp. 552-554.

(Continued)

*Primary Examiner* — Catherine Hibbert
(74) *Attorney, Agent, or Firm* — Ping Wang; Andrews Kurth LLP

(57) ABSTRACT

Disclosed are: transcription regulatory factors capable of regulating the transcription or expression of genes for mannanases or cellulases, as mentioned below; and others. Specifically disclosed is a protein selected from the following proteins (a), (b) and (c): (a) a protein comprising the amino acid sequence depicted in SEQ ID NO:2; (b) a protein which comprises an amino acid sequence produced by deleting, substituting or adding one or several amino acid residues (e.g., 1 to 5 amino acid residues) in the amino acid sequence depicted in SEQ ID NO:2 and which is capable of regulating the transcription of genes for mannanases or cellulases; and (c) a protein which comprises an amino acid sequence having a 70% or higher sequence identity to the amino acid sequence depicted in SEQ ID NO:2 and which is capable of regulating the transcription of genes for mannanases or cellulases, or a partial fragment of the protein. Also specifically disclosed are a gene encoding the protein, and others.

6 Claims, 14 Drawing Sheets

(56) References Cited

OTHER PUBLICATIONS

Arcand, N., et al., "β-Mannanase of Streptomyces lividans 66: cloning and DNA sequence of the manA gene and characterization of the enzyme", Biochem. J (1993) 290, pp. 857-863.

Braithwaite, K., et al., "A non-modular endo-β-1,4-mannanase from Pseudomonas fluorescens subspecies cellulosa", Biochem. J (1995) 305, pp. 1005-1010.

Civas, A., et al., "Glycosidases induced in *Aspergillus tarnarii*", Biochem. J (1984) 219, pp. 857-863.

Hashem, A.M., et al., "Production and properties of β-mannanase by free and immobilized cells of *Aspergillus oryzae* NRRL 3488", Cytobios (2001) 105, pp. 115-130.

Sadaie, Y., et al., "Glucomannan utilization operon of *Bacillus subtilis*", FEMS Microbiol Lett (2008) 279, pp. 103-109.

Supplementary European Search Report of Application No. EP 10 74 8724 mailed Jan. 30, 2013.

"Subname: Full=C6 transcription factor, putative", XP002690332, Mar. 3, 2009, retrieved from EBI accession No. UNIPROT:B8NVU5.

Ogawa, M. et al., "ManR, a novel Zn(II)2Cys6 transcriptional activator, controls the β-mannan utilization system in *Aspergillus oryzae*", Fungal Genetics and Biology, Dec. 2012, vol. 49, pp. 987-995.

* cited by examiner

Figure 1
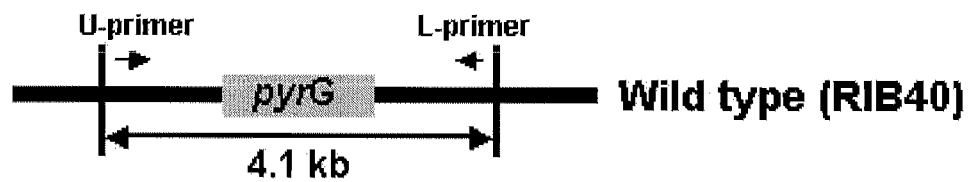
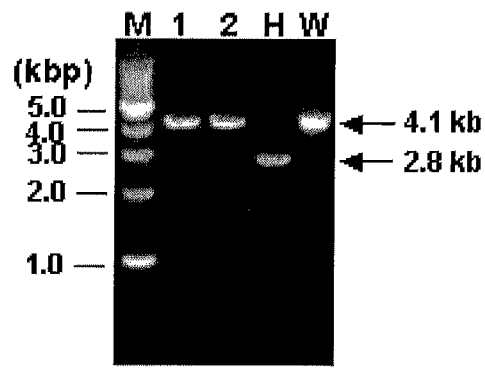
Figure 2
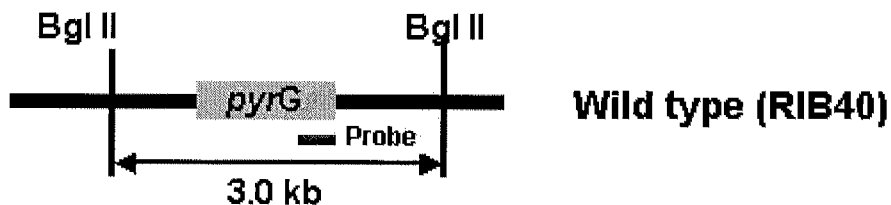
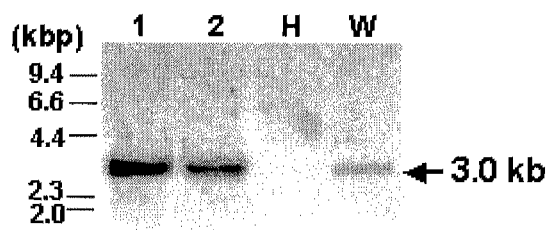

1: ΔmanR x-1-3
2: ΔmanR x-3-2
3: Parent (Host)

Figure 8

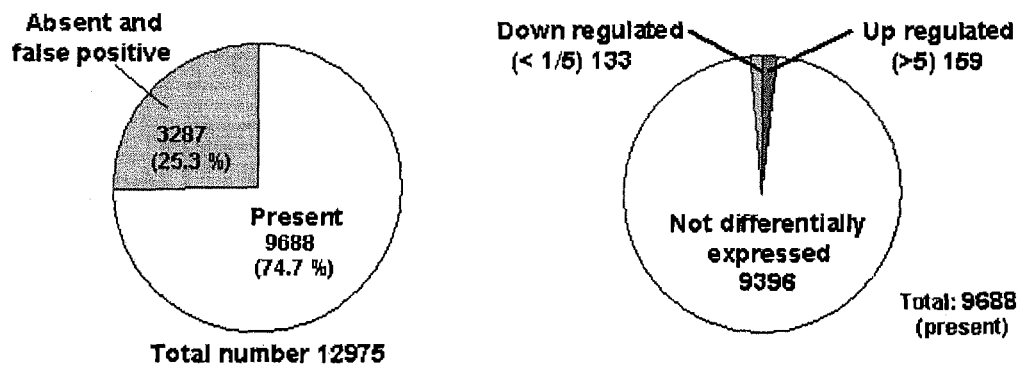

Total number 12975    Total: 9688 (present)

Figure 9

| Gene ID | P and A | Annotation | Ratio | St div |
|---|---|---|---|---|
| AO090038000445 | P | predicted protein | 0.0227 | 0.0107 |
| AO090011000152 | P | phosphoglycerate mutase | 0.0339 | 0.0129 |
| AO090001000571 | P | NADP/FAD dependent oxidoreductase | 0.0364 | 0.0034 |
| AO090005000740 | P | beta-mannosidase/beta-galactosidase (GH family 2) | 0.0371 | 0.0190 |
| AO090010000122 | P | endo-beta-mannanase (GH family 5) | 0.0410 | 0.0135 |
| AO090003000854 | P | urea transporter | 0.0434 | 0.0105 |
| AO090020000141 | P | predicted transporter (major facilitator superfamily) | 0.0470 | 0.0140 |
| AO090003001305 | P | alpha-D-galactosidase (melibiase) (GH family 27) | 0.0480 | 0.0154 |
| AO090038000444 | P | endo-beta-mannanase (GH family 5) | 0.0537 | 0.0161 |
| AO090023000923 | P | glutamate/leucine/phenylalanine/valine dehydrogenases | 0.0541 | 0.0232 |
| AO090010000208 | P | beta-mannosidase/beta-galactosidase (GH family 2) | 0.0562 | 0.0361 |
| AO090003001406 | P | predicted protein | 0.0574 | 0.0104 |
| AO090011000100 | P | predicted protein | 0.0596 | 0.0316 |
| AO090001000348 | P | CelC, cellobiohydrolase (GH familly 7) | 0.0624 | 0.0120 |
| AO090005000743 | P | predicted transporter (major facilitator superfamily) | 0.0635 | 0.0198 |
| AO090003000497 | P | beta-glucosidase/lactase (GH family 1) | 0.0637 | 0.0350 |
| AO090138000025 | P | predicted protein | 0.0639 | 0.0568 |
| AO090001000617 | P | predicted protein | 0.0642 | 0.0400 |
| AO090020000195 | P | predicted protein | 0.0651 | 0.0331 |
| AO090010000562 | P | predicted protein | 0.0657 | 0.0197 |
| AO090113000105 | P | predicted protein | 0.0661 | 0.0168 |
| AO090103000421 | P | permease of the major facilitator superfamily | 0.0685 | 0.0114 |
| AO090020000347 | P | phosphoadenosine phosphosulfate reductase | 0.0709 | 0.0141 |
| AO090005000583 | P | predicted protein | 0.0725 | 0.0458 |
| AO090701000738 | P | predicted protein | 0.0738 | 0.0614 |

M: 1kbp ladder
1: $P_{TEF1}$-manR 1-1-1
2: $P_{TEF1}$-manR 2-1-2
3: Parent (Host)

Figure 20
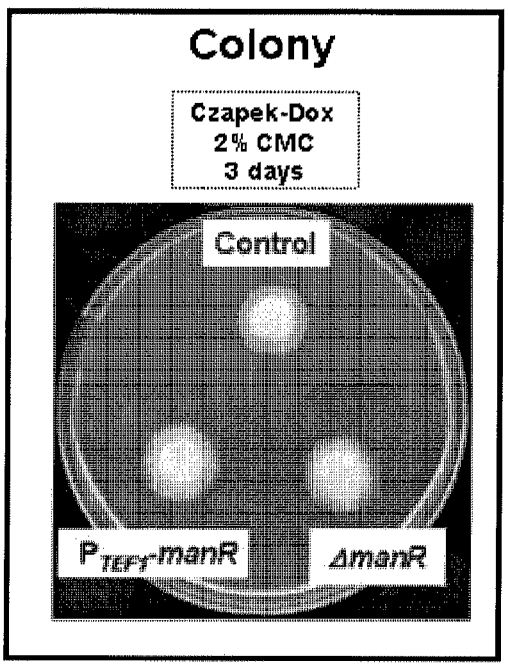 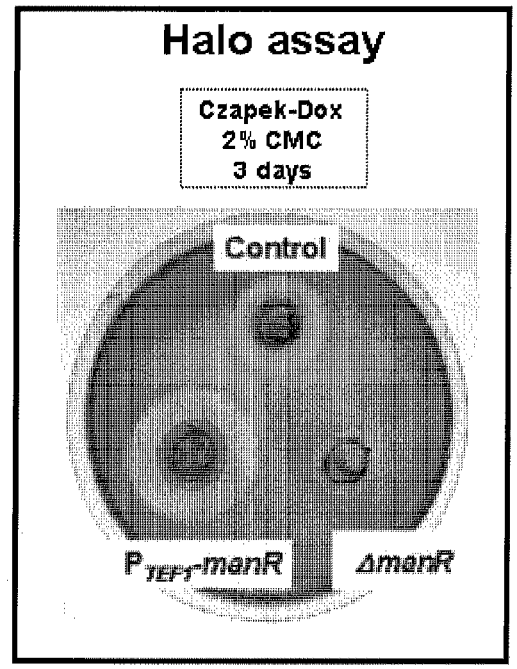

Figure 21

| Avicel 6h (manR disruptiaon and overexpression) | | manR Disruption | | | manR Overexpression | | |
|---|---|---|---|---|---|---|---|
| Gene ID | Annotation | Ratio | p-value | Flags | Ratio | p-value | Flags |
| AO090005000252 | Predicted protein | 0.0499 | 2.39E-06 | P,A | 14.480 | 1.31E-04 | A |
| AO090012000941 | Cellobiohydrolase D (GH family 7) | 0.0580 | 1.14E-06 | P,A | 11.840 | 4.19E-05 | P,A |
| AO090102000458 | Predicted protein | 0.0674 | 4.21E-05 | P | 12.960 | 4.23E-05 | P |
| AO090005001552 | Carbohydrate exterase (CE family16) | 0.0647 | 9.18E-07 | P | 10.890 | 5.54E-08 | P |
| AO090010000562 | β-xylosidase, α-L-arabinofuranosidase | 0.0733 | 1.00E-07 | P | 11.460 | 7.57E-06 | P |
| AO090009000139 | Methylenetetrahydrofolate dehydroger | 0.0927 | 9.68E-06 | P | 9.138 | 3.40E-05 | P |
| AO090113000105 | Endo-1,3(4)-β-glucanase (GH family16) | 0.0830 | 1.27E-06 | P | 10.300 | 3.50E-05 | P |
| AO090010000684 | α-galactosidase (GH family 36) | 0.0866 | 4.84E-06 | P | 10.260 | 2.27E-06 | P |
| AO090005000740 | β-mannosidase (GH family 2) | 0.0401 | 2.89E-06 | P | 24.530 | 2.20E-04 | P |
| AO090003001305 | α-D-galactosidase (melibiase) (GH fam | 0.0651 | 2.34E-05 | P | 13.710 | 6.98E-05 | P |
| AO090003_ig94 | Predicted protein (mannual annotation | 0.0164 | 1.08E-04 | P | 58.550 | 1.34E-04 | P |
| AO090038000439 | Cellobiohydrolase A (GH family 6) | 0.0893 | 1.57E-04 | P | 10.440 | 1.92E-04 | P |
| AO090003000497 | β-glucosidase (GH family 1) | 0.0890 | 1.18E-06 | P | 8.691 | 8.95E-05 | P |
| AO090020000141 | Predicted transporter (major facilitator: | 0.0714 | 4.94E-06 | P | 11.650 | 5.77E-05 | P |
| AO090010_ig12 | manR (Zn$_2$Cys$_6$ zinc finger) | 0.0806 | 5.40E-05 | P | 12.520 | 2.19E-05 | P |
| AO090038000444 | Endo-β-mannanase (GH family 5) | 0.0517 | 6.45E-05 | P | 19.360 | 6.97E-05 | P |
| AO090005001553 | Endoglucanase (GH family 5) | 0.0324 | 2.09E-06 | P | 28.440 | 2.09E-06 | P |
| AO090010000208 | β-mannosidase (GH family 2) | 0.0963 | 1.45E-05 | P | 8.186 | 3.09E-04 | P |
| AO090009000140 | Uncharacterized protein conserved in | 0.0831 | 1.19E-04 | P | 10.260 | 9.81E-05 | P |
| AO090010000122 | Endo-β-mannanase (GH family 5) | 0.0290 | 4.41E-04 | P | 31.810 | 7.12E-04 | P |
| AO090009_ig23 | Predicted protein (mannual annotation | 0.0891 | 4.72E-06 | P | 10.800 | 6.61E-04 | P |
| AO090038000445 | Predicted protein | 0.0297 | 2.36E-05 | P | 32.330 | 3.35E-04 | P |
| AO090001000348 | Cellobiohydrolase C (GH family 7) | 0.0291 | 4.16E-04 | P | 33.010 | 6.14E-04 | P |

Figure 22

| AO090001000348 | Cellobiohydrolase C (CelC) (GH Family | 0.2060 | 7.99E-06 | 8.627 | 1.28E-04 |
|---|---|---|---|---|---|
| AO090003_ig94 | Predicted protein | 0.0989 | 4.23E-04 | 6.166 | 2.23E-05 |
| AO090003000905 | Endoglucanase (GH Family 12) | 0.1750 | 1.17E-03 | 2.698 | 8.68E-04 |
| AO090003001305 | Alpha-D-galactosidase (melibiase) (GH | 0.1340 | 1.51E-03 | 1.408 | 1.88E-02 |
| AO090005000252 | Predicted protein | 0.1690 | 1.77E-03 | 1.249 | 1.45E-01 |
| AO090005000740 | Beta-mannosidase/galactosidase (GH F | 0.1590 | 4.06E-04 | 2.409 | 1.65E-03 |
| AO090005000743 | Predicted transporter (major facilitator | 0.1550 | 1.22E-05 | 2.012 | 2.20E-03 |
| AO090005001552 | Predicted protein | 0.0836 | 2.96E-04 | 2.627 | 4.97E-03 |
| AO090005001553 | Endoglucanase (GH Family 5) | 0.1170 | 1.85E-04 | 3.103 | 1.14E-03 |
| AO090010_ig12 | manR (Zn-Cys$_6$ transcriptional regulate | 0.1470 | 6.47E-05 | 7.054 | 5.41E-06 |
| AO090010000122 | Endo-beta-mannanase (GH Family 5) | 0.0759 | 5.98E-04 | 7.975 | 2.75E-04 |
| AO090010000208 | Beta-mannosidase/galactosidase (GH F | 0.2350 | 2.47E-04 | 0.895 | 3.35E-01 |
| AO090010000314 | CelB, endo-1,4-beta-glucanase | 0.0948 | 1.31E-03 | 1.847 | 1.37E-02 |
| AO090011000055 | Endo-beta-mannanase (GH Family 26) | 0.2390 | 2.41E-04 | 1.181 | 5.43E-02 |
| AO090011000673 | An Pel-Pectate lyase, pectate lyase | 0.1690 | 4.87E-05 | 5.046 | 1.89E-04 |
| AO090012000941 | Cellobiohydrolase D (CelD) (GH Family | 0.0943 | 1.66E-03 | 1.649 | 5.36E-02 |
| AO090020000141 | Predicted transporter (major facilitator | 0.1490 | 3.63E-04 | 2.308 | 1.74E-03 |
| AO090023000787 | Endoglucanase (GH Family 61) | 0.1490 | 8.69E-04 | 0.742 | 1.15E-01 |
| AO090038000439 | Endoglucanase (GH Family 6) | 0.2300 | 1.43E-03 | 2.244 | 7.68E-03 |
| AO090038000444 | Endo-beta-mannanase (GH Family 5) | 0.1120 | 1.34E-03 | 1.328 | 6.66E-02 |
| AO090038000445 | Predicted protein | 0.0651 | 7.68E-05 | 1.552 | 3.79E-02 |

SEQUENCE LISTING

```
<160> NUMBER OF SEQ ID NOS: 51

<210> SEQ ID NO 1
<211> LENGTH: 2316
<212> TYPE: DNA
<213> ORGANISM: Aspergillus oryzae
<220> FEATURE:
<221> NAME/KEY: CDS
<222> LOCATION: (1)..(2316)
<223> OTHER INFORMATION: manR nucleotide sequence and translation
      product

<400> SEQUENCE: 1 atg ttc cac acc ttt gaa gga ttc gaa aac ccg aac aac tcg gcc cca        48
Met Phe His Thr Phe Glu Gly Phe Glu Asn Pro Asn Asn Ser Ala Pro
1               5                   10                  15 gtc cgg ggt cgt ggt gag cgc cag cca tcc gtc ggc cga cgt gtc act        96
Val Arg Gly Arg Gly Glu Arg Gln Pro Ser Val Gly Arg Arg Val Thr
            20                  25                  30 acc ctt cgt gcc tgt aca tca tgc aga cat cgc aag atc aag tgt gac       144
Thr Leu Arg Ala Cys Thr Ser Cys Arg His Arg Lys Ile Lys Cys Asp
        35                  40                  45 ggt gaa aag ccg tgc gaa gcg tgt cgg tgg tat aag aaa gcc gac cag       192
Gly Glu Lys Pro Cys Glu Ala Cys Arg Trp Tyr Lys Lys Ala Asp Gln
    50                  55                  60 tgt cat tat gca gat ccc cgg ccc tcc cgc aga cat gta gaa aaa ctc       240
Cys His Tyr Ala Asp Pro Arg Pro Ser Arg Arg His Val Glu Lys Leu
65                  70                  75                  80 tcc acc act ttg gac gag tat cgg ggc gtg ctc gag aaa ctc ttc cct       288
Ser Thr Thr Leu Asp Glu Tyr Arg Gly Val Leu Glu Lys Leu Phe Pro
                85                  90                  95 aat atc caa ccc gaa aat tta gtt agc ttg cct cgc gaa aag ctt ttg       336
Asn Ile Gln Pro Glu Asn Leu Val Ser Leu Pro Arg Glu Lys Leu Leu
            100                 105                 110 gag ctg atg ggc aag cca tcc ctg ctg cag aca cag ccg cca cac cca       384
Glu Leu Met Gly Lys Pro Ser Leu Leu Gln Thr Gln Pro Pro His Pro
        115                 120                 125 gcg tca cca gct acc tcg gca tcg gtc gaa gcc cat gtc tcc ccc gtc       432
Ala Ser Pro Ala Thr Ser Ala Ser Val Glu Ala His Val Ser Pro Val
    130                 135                 140 tcc aac gaa gat ggc aat ttg gaa tct ttg cag acg atg cct gaa gaa       480
```

|  |  |  |  |  |  |  |  |  |  |  |  |  |  |  |  |
|---|---|---|---|---|---|---|---|---|---|---|---|---|---|---|---|
| Ser | Asn | Glu | Asp | Gly | Asn | Leu | Glu | Ser | Leu | Gln | Thr | Met | Pro | Glu |  |
| 145 |  |  |  |  | 150 |  |  |  |  | 155 |  |  |  |  | 160 |

```
tcc agt gat tct caa aac tcg ggt tat acg gag ata tcc aat aat ttt      528
Ser Ser Asp Ser Gln Asn Ser Gly Tyr Thr Glu Ile Ser Asn Asn Phe
            165                 170                 175 tcg gac gac gtc aat gct ctg tca ctc tca tcc aga cag ccc tcc tct      576
Ser Asp Asp Val Asn Ala Leu Ser Leu Ser Ser Arg Gln Pro Ser Ser
        180                 185                 190 tat ttg ggc gtg tcg tct atc aat gct gtt ctc aaa gtg att ctc tgc      624
Tyr Leu Gly Val Ser Ser Ile Asn Ala Val Leu Lys Val Ile Leu Cys
        195                 200                 205 ctt gac cct ggc gcc ctc tct tac ttc tct cat ccc tcg acc aac aca      672
Leu Asp Pro Gly Ala Leu Ser Tyr Phe Ser His Pro Ser Thr Asn Thr
210                 215                 220 gac tcc agg gac tca gct cta gga tac tcc cca gca gaa gca caa cca      720
Asp Ser Arg Asp Ser Ala Leu Gly Tyr Ser Pro Ala Glu Ala Gln Pro
225                 230                 235                 240 tgg ccg gtc caa gag tct cag caa cca ata acg ccc cct caa cca cat      768
Trp Pro Val Gln Glu Ser Gln Gln Pro Ile Thr Pro Pro Gln Pro His
            245                 250                 255 cga cca gta aca gag atg cag ttg ctc gac gcc tac ttt act tat ttt      816
Arg Pro Val Thr Glu Met Gln Leu Leu Asp Ala Tyr Phe Thr Tyr Phe
        260                 265                 270 cag cca ttc gtg ccc atg cta gat gag gaa gtt ttc cgc gag gtc tat      864
Gln Pro Phe Val Pro Met Leu Asp Glu Glu Val Phe Arg Glu Val Tyr
        275                 280                 285 cac tcg ggg tgt aga aag gat gaa cgt tgg ctg gca ctg ctg aac att      912
His Ser Gly Cys Arg Lys Asp Glu Arg Trp Leu Ala Leu Leu Asn Ile
        290                 295                 300 gtg ctt gcc ttg ggt agc atc gca gca tgt cca tcg gat gac atg tcc      960
Val Leu Ala Leu Gly Ser Ile Ala Ala Cys Pro Ser Asp Asp Met Ser
305                 310                 315                 320 cac aca att tac gcc cag cgc tgt aag agc tac ttg aat tta gaa tcg     1008
His Thr Ile Tyr Ala Gln Arg Cys Lys Ser Tyr Leu Asn Leu Glu Ser
            325                 330                 335 ctt gga tcc tca cat ata gag acc atc cag act ctc ggc ctt ctg gga     1056
Leu Gly Ser Ser His Ile Glu Thr Ile Gln Thr Leu Gly Leu Leu Gly
        340                 345                 350 ggg cag tat ctt cat tat gtc agt caa ccc aat ctg gca tat tcg ctc     1104
Gly Gln Tyr Leu His Tyr Val Ser Gln Pro Asn Leu Ala Tyr Ser Leu
        355                 360                 365 atg gga gct gcg ctg cgc atg gct gca gct ttg ggc ttg cac aaa gag     1152
Met Gly Ala Ala Leu Arg Met Ala Ala Ala Leu Gly Leu His Lys Glu
370                 375                 380 ttt tca gat aac cag gaa ggg tcg tgt aag cag aac ata tat tcg act     1200
Phe Ser Asp Asn Gln Glu Gly Ser Cys Lys Gln Asn Ile Tyr Ser Thr
385                 390                 395                 400 gac ctg aaa cgg cga gtg tgg tgg tcg ctg ttt tgc ttg gac act tgg     1248
Asp Leu Lys Arg Arg Val Trp Trp Ser Leu Phe Cys Leu Asp Thr Trp
            405                 410                 415 ggc tgt atg act ctg ggg cga ccg agt atg gga cga ttt gga ccg acg     1296
Gly Cys Met Thr Leu Gly Arg Pro Ser Met Gly Arg Phe Gly Pro Thr
        420                 425                 430 att acc gtt aaa ctg ccg cag tac cga gaa aga ggg aat gtt ctc gac     1344
Ile Thr Val Lys Leu Pro Gln Tyr Arg Glu Arg Gly Asn Val Leu Asp
        435                 440                 445 att ata ccg ctt cta gaa aac gtt cgg ttc tgc aaa att gcg aca cag     1392
Ile Ile Pro Leu Leu Glu Asn Val Arg Phe Cys Lys Ile Ala Thr Gln
450                 455                 460
```

```
                                        -continued atc cag gaa att ctg gct gcc gct ccg ttg acg agg tac cac gag atg     1440
Ile Gln Glu Ile Leu Ala Ala Ala Pro Leu Thr Arg Tyr His Glu Met
465             470                 475                 480 tcg cac ttt gat aat caa ctg tta gag tgg tat gag aac ctt ccg tat     1488
Ser His Phe Asp Asn Gln Leu Leu Glu Trp Tyr Glu Asn Leu Pro Tyr
                485                 490                 495 ata ctc aaa gac cac gag cca tgc tcc gaa tca att atc atc acc agg     1536
Ile Leu Lys Asp His Glu Pro Cys Ser Glu Ser Ile Ile Ile Thr Arg
            500                 505                 510 aca gtc atg aaa tgg cgg tac tac aac cag cgt atg ctc ata tac cgt     1584
Thr Val Met Lys Trp Arg Tyr Tyr Asn Gln Arg Met Leu Ile Tyr Arg
        515                 520                 525 cca act cta ctc agc tac gcc atg cgg cgg gtt cca tat att gct ctc     1632
Pro Thr Leu Leu Ser Tyr Ala Met Arg Arg Val Pro Tyr Ile Ala Leu
    530                 535                 540 cgt tcc gaa gag cgg acg gcg atc gaa agg tgt cga cag atc gcg gag     1680
Arg Ser Glu Glu Arg Thr Ala Ile Glu Arg Cys Arg Gln Ile Ala Glu
545                 550                 555                 560 gct aca att caa gac att tct tca acg gcc cag tca cat caa atg tcg     1728
Ala Thr Ile Gln Asp Ile Ser Ser Thr Ala Gln Ser His Gln Met Ser
                565                 570                 575 ggc tgg agt gca gtc tgg ctc ata ttc cag gca gtc atg gtt ccc cta     1776
Gly Trp Ser Ala Val Trp Leu Ile Phe Gln Ala Val Met Val Pro Leu
            580                 585                 590 ttg gga ttg ttt ctc aac gac aac aca acg agt gac cct aga gct act     1824
Leu Gly Leu Phe Leu Asn Asp Asn Thr Thr Ser Asp Pro Arg Ala Thr
        595                 600                 605 gtt gcg agc tgc caa tct caa gtt gag atg gct atg ctt gtc ctg gcc     1872
Val Ala Ser Cys Gln Ser Gln Val Glu Met Ala Met Leu Val Leu Ala
    610                 615                 620 cga ctg gaa caa tgg agc ccg act gca aaa agg acg ttg ggt gcc gta     1920
Arg Leu Glu Gln Trp Ser Pro Thr Ala Lys Arg Thr Leu Gly Ala Val
625                 630                 635                 640 tcg cag ata ttg gaa gct agt aag aga ggg act aac atg gcc aac gag     1968
Ser Gln Ile Leu Glu Ala Ser Lys Arg Gly Thr Asn Met Ala Asn Glu
                645                 650                 655 gct ggc ctt gtc aat agc atg ttt gct gtc tca cgc gag ggg gca gtg     2016
Ala Gly Leu Val Asn Ser Met Phe Ala Val Ser Arg Glu Gly Ala Val
            660                 665                 670 cct cga gcc gct tca ggg ttt cat ccg tcc caa aac att ttc ctt cag     2064
Pro Arg Ala Ala Ser Gly Phe His Pro Ser Gln Asn Ile Phe Leu Gln
        675                 680                 685 aat gag gca ggc ttt gat ccg ttt gcg cct cca gtt att gac gac tcg     2112
Asn Glu Ala Gly Phe Asp Pro Phe Ala Pro Pro Val Ile Asp Asp Ser
    690                 695                 700 acg gct cag tac cta tgg gac ttc ttg agc tgg agc gat agc agc cta     2160
Thr Ala Gln Tyr Leu Trp Asp Phe Leu Ser Trp Ser Asp Ser Ser Leu
705                 710                 715                 720 tgg cct gga ata acg gac acc aat agc ttc aac gac gaa acg ctg ttc     2208
Trp Pro Gly Ile Thr Asp Thr Asn Ser Phe Asn Asp Glu Thr Leu Phe
                725                 730                 735 gcc caa aca gac aaa acc atg aaa tat ccc aac aac ggt gca gcc ttt     2256
Ala Gln Thr Asp Lys Thr Met Lys Tyr Pro Asn Asn Gly Ala Ala Phe
            740                 745                 750 atg ggg ggc tct atg gga gac ggt gcc tac tat gca aat cca cct ttg     2304
Met Gly Gly Ser Met Gly Asp Gly Ala Tyr Tyr Ala Asn Pro Pro Leu
        755                 760                 765 ccc tac tac taa                                                     2316
Pro Tyr Tyr
    770
```

<210> SEQ ID NO 2
<211> LENGTH: 771
<212> TYPE: PRT
<213> ORGANISM: Aspergillus oryzae

<400> SEQUENCE: 2

```
Met Phe His Thr Phe Glu Gly Phe Glu Asn Pro Asn Ser Ala Pro
1               5                   10                  15

Val Arg Gly Arg Gly Glu Arg Gln Pro Ser Val Gly Arg Val Thr
                20                  25                  30

Thr Leu Arg Ala Cys Thr Ser Cys Arg His Arg Lys Ile Lys Cys Asp
                35                  40                  45

Gly Glu Lys Pro Cys Glu Ala Cys Arg Trp Tyr Lys Lys Ala Asp Gln
    50                  55                  60

Cys His Tyr Ala Asp Pro Arg Pro Ser Arg Arg His Val Glu Lys Leu
65                  70                  75                  80

Ser Thr Thr Leu Asp Glu Tyr Arg Gly Val Leu Glu Lys Leu Phe Pro
                85                  90                  95

Asn Ile Gln Pro Glu Asn Leu Val Ser Leu Pro Arg Glu Lys Leu Leu
                100                 105                 110

Glu Leu Met Gly Lys Pro Ser Leu Leu Gln Thr Gln Pro Pro His Pro
            115                 120                 125

Ala Ser Pro Ala Thr Ser Ala Ser Val Glu Ala His Val Ser Pro Val
    130                 135                 140

Ser Asn Glu Asp Gly Asn Leu Glu Ser Leu Gln Thr Met Pro Glu Glu
145                 150                 155                 160

Ser Ser Asp Ser Gln Asn Ser Gly Tyr Thr Glu Ile Ser Asn Asn Phe
                165                 170                 175

Ser Asp Asp Val Asn Ala Leu Ser Leu Ser Ser Arg Gln Pro Ser Ser
                180                 185                 190

Tyr Leu Gly Val Ser Ser Ile Asn Ala Val Leu Lys Val Ile Leu Cys
            195                 200                 205

Leu Asp Pro Gly Ala Leu Ser Tyr Phe Ser His Pro Ser Thr Asn Thr
210                 215                 220

Asp Ser Arg Asp Ser Ala Leu Gly Tyr Ser Pro Ala Glu Ala Gln Pro
225                 230                 235                 240

Trp Pro Val Gln Glu Ser Gln Gln Pro Ile Thr Pro Gln Pro His
                245                 250                 255

Arg Pro Val Thr Glu Met Gln Leu Leu Asp Ala Tyr Phe Thr Tyr Phe
            260                 265                 270

Gln Pro Phe Val Pro Met Leu Asp Glu Glu Val Phe Arg Glu Val Tyr
        275                 280                 285

His Ser Gly Cys Arg Lys Asp Glu Arg Trp Leu Ala Leu Leu Asn Ile
    290                 295                 300

Val Leu Ala Leu Gly Ser Ile Ala Ala Cys Pro Ser Asp Asp Met Ser
305                 310                 315                 320

His Thr Ile Tyr Ala Gln Arg Cys Lys Ser Tyr Leu Asn Leu Glu Ser
                325                 330                 335

Leu Gly Ser Ser His Ile Glu Thr Ile Gln Thr Leu Gly Leu Leu Gly
            340                 345                 350

Gly Gln Tyr Leu His Tyr Val Ser Gln Pro Asn Leu Ala Tyr Ser Leu
        355                 360                 365

Met Gly Ala Ala Leu Arg Met Ala Ala Ala Leu Gly Leu His Lys Glu
```

```
               370                 375                 380
Phe Ser Asp Asn Gln Glu Gly Ser Cys Lys Gln Asn Ile Tyr Ser Thr
385                 390                 395                 400

Asp Leu Lys Arg Arg Val Trp Trp Ser Leu Phe Cys Leu Asp Thr Trp
                405                 410                 415

Gly Cys Met Thr Leu Gly Arg Pro Ser Met Gly Arg Phe Gly Pro Thr
            420                 425                 430

Ile Thr Val Lys Leu Pro Gln Tyr Arg Glu Arg Gly Asn Val Leu Asp
                435                 440                 445

Ile Ile Pro Leu Leu Glu Asn Val Arg Phe Cys Lys Ile Ala Thr Gln
            450                 455                 460

Ile Gln Glu Ile Leu Ala Ala Pro Leu Thr Arg Tyr His Glu Met
465                 470                 475                 480

Ser His Phe Asp Asn Gln Leu Leu Glu Trp Tyr Glu Asn Leu Pro Tyr
                485                 490                 495

Ile Leu Lys Asp His Glu Pro Cys Ser Glu Ser Ile Ile Ile Thr Arg
            500                 505                 510

Thr Val Met Lys Trp Arg Tyr Tyr Asn Gln Arg Met Leu Ile Tyr Arg
                515                 520                 525

Pro Thr Leu Leu Ser Tyr Ala Met Arg Arg Val Pro Tyr Ile Ala Leu
        530                 535                 540

Arg Ser Glu Glu Arg Thr Ala Ile Glu Arg Cys Arg Gln Ile Ala Glu
545                 550                 555                 560

Ala Thr Ile Gln Asp Ile Ser Ser Thr Ala Gln Ser His Gln Met Ser
                565                 570                 575

Gly Trp Ser Ala Val Trp Leu Ile Phe Gln Ala Val Met Val Pro Leu
            580                 585                 590

Leu Gly Leu Phe Leu Asn Asp Asn Thr Thr Ser Asp Pro Arg Ala Thr
                595                 600                 605

Val Ala Ser Cys Gln Ser Gln Val Glu Met Ala Met Leu Val Leu Ala
        610                 615                 620

Arg Leu Glu Gln Trp Ser Pro Thr Ala Lys Arg Thr Leu Gly Ala Val
625                 630                 635                 640

Ser Gln Ile Leu Glu Ala Ser Lys Arg Gly Thr Asn Met Ala Asn Glu
                645                 650                 655

Ala Gly Leu Val Asn Ser Met Phe Ala Val Ser Arg Glu Gly Ala Val
            660                 665                 670

Pro Arg Ala Ala Ser Gly Phe His Pro Ser Gln Asn Ile Phe Leu Gln
                675                 680                 685

Asn Glu Ala Gly Phe Asp Pro Phe Ala Pro Val Ile Asp Asp Ser
        690                 695                 700

Thr Ala Gln Tyr Leu Trp Asp Phe Leu Ser Trp Ser Asp Ser Ser Leu
705                 710                 715                 720

Trp Pro Gly Ile Thr Asp Thr Asn Ser Phe Asn Asp Glu Thr Leu Phe
                725                 730                 735

Ala Gln Thr Asp Lys Thr Met Lys Tyr Pro Asn Asn Gly Ala Ala Phe
            740                 745                 750

Met Gly Gly Ser Met Gly Asp Gly Ala Tyr Tyr Ala Asn Pro Pro Leu
            755                 760                 765

Pro Tyr Tyr
    770

<210> SEQ ID NO 3
```

```
<211> LENGTH: 26
<212> TYPE: DNA
<213> ORGANISM: Artificial Sequence
<220> FEATURE:
<223> OTHER INFORMATION: Primer

<400> SEQUENCE: 3
acgtgtgcag gtctcggaca aaacac                                              26

<210> SEQ ID NO 4
<211> LENGTH: 28
<212> TYPE: DNA
<213> ORGANISM: Artificial Sequence
<220> FEATURE:
<223> OTHER INFORMATION: Primer

<400> SEQUENCE: 4
cctcccgcct ctatcgacaa ataatatg                                            28

<210> SEQ ID NO 5
<211> LENGTH: 26
<212> TYPE: DNA
<213> ORGANISM: Artificial Sequence
<220> FEATURE:
<223> OTHER INFORMATION: Primer

<400> SEQUENCE: 5
cgtacattgc cgtgatcaaa actcac                                              26

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
gtcacccttc gaggagaggt tgacac                                              26

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7
aggtgacctg caatttcaat aaactttg                                            28

<210> SEQ ID NO 8
<211> LENGTH: 38
<212> TYPE: DNA
<213> ORGANISM: Artificial Sequence
<220> FEATURE:
<223> OTHER INFORMATION: Primer

<400> SEQUENCE: 8
gtacgtctgt tgtcagccga gtccagggat tttttctg                                 38

<210> SEQ ID NO 9
<211> LENGTH: 44
<212> TYPE: DNA
<213> ORGANISM: Artificial Sequence
<220> FEATURE:
<223> OTHER INFORMATION: Primer

<400> SEQUENCE: 9
```

```
aaatccctgg actcggctga caacagacgt accctgtgat gttc          44
```

<210> SEQ ID NO 10
<211> LENGTH: 47
<212> TYPE: DNA
<213> ORGANISM: Artificial Sequence
<220> FEATURE:
<223> OTHER INFORMATION: Primer

<400> SEQUENCE: 10

```
tggacggtat atgagcatac gcaactgcac ctcagaagaa aaggatg        47
```

<210> SEQ ID NO 11
<211> LENGTH: 42
<212> TYPE: DNA
<213> ORGANISM: Artificial Sequence
<220> FEATURE:
<223> OTHER INFORMATION: Primer

<400> SEQUENCE: 11

```
ctgaggtgca gttgcgtatg ctcatatacc gtccaactct ac            42
```

<210> SEQ ID NO 12
<211> LENGTH: 29
<212> TYPE: DNA
<213> ORGANISM: Artificial Sequence
<220> FEATURE:
<223> OTHER INFORMATION: Primer

<400> SEQUENCE: 12

```
cgtatggtga atcacccttt gaaacatac                           29
```

<210> SEQ ID NO 13
<211> LENGTH: 26
<212> TYPE: DNA
<213> ORGANISM: Artificial Sequence
<220> FEATURE:
<223> OTHER INFORMATION: Primer

<400> SEQUENCE: 13

```
atgaacgggg cgatgttcct taatac                              26
```

<210> SEQ ID NO 14
<211> LENGTH: 26
<212> TYPE: DNA
<213> ORGANISM: Artificial Sequence
<220> FEATURE:
<223> OTHER INFORMATION: Primer

<400> SEQUENCE: 14

```
gcatacctga gcgatgaccc atagag                              26
```

<210> SEQ ID NO 15
<211> LENGTH: 27
<212> TYPE: DNA
<213> ORGANISM: Artificial Sequence
<220> FEATURE:
<223> OTHER INFORMATION: Primer

<400> SEQUENCE: 15

```
ctactgttgc gagctgccaa tctcaag                             27
```

<210> SEQ ID NO 16
<211> LENGTH: 27
<212> TYPE: DNA

```
<213> ORGANISM: Artificial Sequence
<220> FEATURE:
<223> OTHER INFORMATION: Primer

<400> SEQUENCE: 16
ccgttgttgg gatatttcat ggttttg                                              27

<210> SEQ ID NO 17
<211> LENGTH: 44
<212> TYPE: DNA
<213> ORGANISM: Artificial Sequence
<220> FEATURE:
<223> OTHER INFORMATION: Primer

<400> SEQUENCE: 17
aagatctaaa aaaaaatga aattccgtaa cctttctttt gctg                            44

<210> SEQ ID NO 18
<211> LENGTH: 33
<212> TYPE: DNA
<213> ORGANISM: Artificial Sequence
<220> FEATURE:
<223> OTHER INFORMATION: Primer

<400> SEQUENCE: 18
cctcgagccc caggtatgcc tgcagaacgt cca                                       33

<210> SEQ ID NO 19
<211> LENGTH: 42
<212> TYPE: DNA
<213> ORGANISM: Artificial Sequence
<220> FEATURE:
<223> OTHER INFORMATION: Primer

<400> SEQUENCE: 19
gggatccaaa aaaaaatga agcttaaccc ttcactcctc ac                              42

<210> SEQ ID NO 20
<211> LENGTH: 34
<212> TYPE: DNA
<213> ORGANISM: Artificial Sequence
<220> FEATURE:
<223> OTHER INFORMATION: Primer

<400> SEQUENCE: 20
cctcgagctt acgactgttg atggccgcaa tatg                                      34

<210> SEQ ID NO 21
<211> LENGTH: 45
<212> TYPE: DNA
<213> ORGANISM: Artificial Sequence
<220> FEATURE:
<223> OTHER INFORMATION: Primer

<400> SEQUENCE: 21
cggatccaaa aaaaaatgg cggcattctc tcagtaccct ctatc                           45

<210> SEQ ID NO 22
<211> LENGTH: 37
<212> TYPE: DNA
<213> ORGANISM: Artificial Sequence
<220> FEATURE:
<223> OTHER INFORMATION: Primer

<400> SEQUENCE: 22
cctcgagctg gccaagatac ttgtacttca gaggagc                                   37
```

<210> SEQ ID NO 23
<211> LENGTH: 45
<212> TYPE: DNA
<213> ORGANISM: Artificial Sequence
<220> FEATURE:
<223> OTHER INFORMATION: Primer

<400> SEQUENCE: 23
cggatccaaa aaaaaaatgt ccggcttcaa gtcgctcgag ctctc        45

<210> SEQ ID NO 24
<211> LENGTH: 36
<212> TYPE: DNA
<213> ORGANISM: Artificial Sequence
<220> FEATURE:
<223> OTHER INFORMATION: Primer

<400> SEQUENCE: 24
cgtcgactag tctgtcatcc ccaatgtatg tccaac        36

<210> SEQ ID NO 25
<211> LENGTH: 45
<212> TYPE: DNA
<213> ORGANISM: Artificial Sequence
<220> FEATURE:
<223> OTHER INFORMATION: Primer

<400> SEQUENCE: 25
cggatccaaa aaaaaaatgc agcgttacat ttctttatcc gtgtc        45

<210> SEQ ID NO 26
<211> LENGTH: 36
<212> TYPE: DNA
<213> ORGANISM: Artificial Sequence
<220> FEATURE:
<223> OTHER INFORMATION: Primer

<400> SEQUENCE: 26
cctcgaggca tgattctccc accaccagag cagcaa        36

<210> SEQ ID NO 27
<211> LENGTH: 30
<212> TYPE: DNA
<213> ORGANISM: Artificial Sequence
<220> FEATURE:
<223> OTHER INFORMATION: Primer

<400> SEQUENCE: 27
aatctgcagg gtctcacttc tagtacgctg        30

<210> SEQ ID NO 28
<211> LENGTH: 27
<212> TYPE: DNA
<213> ORGANISM: Artificial Sequence
<220> FEATURE:
<223> OTHER INFORMATION: Primer

<400> SEQUENCE: 28
ccgtcacact tgatcttgcg atgtctg        27

<210> SEQ ID NO 29
<211> LENGTH: 30
<212> TYPE: DNA
<213> ORGANISM: Artificial Sequence
<220> FEATURE:

```
<223> OTHER INFORMATION: Primer

<400> SEQUENCE: 29
agctgagtgg gtgtcttctg tttatcattg                                   30

<210> SEQ ID NO 30
<211> LENGTH: 28
<212> TYPE: DNA
<213> ORGANISM: Artificial Sequence
<220> FEATURE:
<223> OTHER INFORMATION: Primer

<400> SEQUENCE: 30
gcatctctgt tactggtcga tgtggttg                                     28

<210> SEQ ID NO 31
<211> LENGTH: 30
<212> TYPE: DNA
<213> ORGANISM: Artificial Sequence
<220> FEATURE:
<223> OTHER INFORMATION: Primer

<400> SEQUENCE: 31
acagactcca gggactcagc tctaggatac                                   30

<210> SEQ ID NO 32
<211> LENGTH: 27
<212> TYPE: DNA
<213> ORGANISM: Artificial Sequence
<220> FEATURE:
<223> OTHER INFORMATION: Primer

<400> SEQUENCE: 32
aacttgagat tggcagctcg caacagt                                      27

<210> SEQ ID NO 33
<211> LENGTH: 29
<212> TYPE: DNA
<213> ORGANISM: Artificial Sequence
<220> FEATURE:
<223> OTHER INFORMATION: Primer

<400> SEQUENCE: 33
gaggctacaa ttcaagacat ttcttcaac                                    29

<210> SEQ ID NO 34
<211> LENGTH: 28
<212> TYPE: DNA
<213> ORGANISM: Artificial Sequence
<220> FEATURE:
<223> OTHER INFORMATION: Primer

<400> SEQUENCE: 34
aaactgatga tcattcatac actatatg                                     28

<210> SEQ ID NO 35
<211> LENGTH: 30
<212> TYPE: DNA
<213> ORGANISM: Artificial Sequence
<220> FEATURE:
<223> OTHER INFORMATION: Primer

<400> SEQUENCE: 35
agctgagtgg gtgtcttctg tttatcattg                                   30
```

```
<210> SEQ ID NO 36
<211> LENGTH: 28
<212> TYPE: DNA
<213> ORGANISM: Artificial Sequence
<220> FEATURE:
<223> OTHER INFORMATION: Primer

<400> SEQUENCE: 36
tagtgccctt aaccagaagg gctagatg                                    28

<210> SEQ ID NO 37
<211> LENGTH: 28
<212> TYPE: DNA
<213> ORGANISM: Artificial Sequence
<220> FEATURE:
<223> OTHER INFORMATION: Primer

<400> SEQUENCE: 37
tgagttaagc gccatgaggg agtatgtc                                    28

<210> SEQ ID NO 38
<211> LENGTH: 41
<212> TYPE: DNA
<213> ORGANISM: Artificial Sequence
<220> FEATURE:
<223> OTHER INFORMATION: Primer

<400> SEQUENCE: 38
gtacgtctgt tgtacgccag gtgaggagtt tacgaggata c                     41

<210> SEQ ID NO 39
<211> LENGTH: 44
<212> TYPE: DNA
<213> ORGANISM: Artificial Sequence
<220> FEATURE:
<223> OTHER INFORMATION: Primer

<400> SEQUENCE: 39
taaactcctc acctggcgta caacagacgt accctgtgat gttc                  44

<210> SEQ ID NO 40
<211> LENGTH: 44
<212> TYPE: DNA
<213> ORGANISM: Artificial Sequence
<220> FEATURE:
<223> OTHER INFORMATION: Primer

<400> SEQUENCE: 40
tgttgacaga ctacggataa actgcacctc agaagaaaag gatg                  44

<210> SEQ ID NO 41
<211> LENGTH: 43
<212> TYPE: DNA
<213> ORGANISM: Artificial Sequence
<220> FEATURE:
<223> OTHER INFORMATION: Primer

<400> SEQUENCE: 41
ctgaggtgca gtttatccgt agtctgtcaa cattgcctct ttg                   43

<210> SEQ ID NO 42
<211> LENGTH: 47
<212> TYPE: DNA
<213> ORGANISM: Artificial Sequence
<220> FEATURE:
<223> OTHER INFORMATION: Primer
```

<400> SEQUENCE: 42
aatcgatcag aaccggccaa cacaactcga cgggttgata aacttac           47

<210> SEQ ID NO 43
<211> LENGTH: 42
<212> TYPE: DNA
<213> ORGANISM: Artificial Sequence
<220> FEATURE:
<223> OTHER INFORMATION: Primer

<400> SEQUENCE: 43
cgtcgagttg tgttggccgg ttctgatcga tttggatcta ag               42

<210> SEQ ID NO 44
<211> LENGTH: 28
<212> TYPE: DNA
<213> ORGANISM: Artificial Sequence
<220> FEATURE:
<223> OTHER INFORMATION: Primer

<400> SEQUENCE: 44
atccataccg tgcccttttcc taaaagac                              28

<210> SEQ ID NO 45
<211> LENGTH: 2487
<212> TYPE: DNA
<213> ORGANISM: Aspergillus oryzae

<400> SEQUENCE: 45

| | |
|---|---|
| atgttccaca cctttgaagg attcgaaaac ccgaacaact cggccccagt ccggggtcgt | 60 |
| ggtgagcgcc agccatccgt cggccgacgt gtcactaccc ttcgtgcctg tacatcatgc | 120 |
| agacatcgca agatcaagtg tgacggtgaa aagccgtgcg aagcgtgtcg gtggtataag | 180 |
| aaagccgacc agtgtcatta tgcagatccc cggccctccc gcaggtgggt tgctctcttt | 240 |
| cttttttgat ttttaattag agataaatgc cccttcttcc ccacagttat ctccccaccc | 300 |
| agacggtgga agatctatac atggcttacg tgggaatgaa aatgcagaca tgtagaaaaa | 360 |
| ctctccacca ctttggacga gtatcggggc gtgctcgaga aactcttccc taatatccaa | 420 |
| cccgaaaatt tagttagctt gcctcgcgaa aagcttttgg agctgatggg caagccatcc | 480 |
| ctgctgcaga cacagccgcc acacccagcg tcaccagcta cctcggcatc ggtcgaagcc | 540 |
| catgtctccc ccgtctccaa cgaagatggc aatttggaat ctttgcagac gatgcctgaa | 600 |
| gaatccagtg attctcaaaa ctcgggttat acggagatat ccaataattt ttcggacgac | 660 |
| gtcaatgctc tgtcactctc atccagacag ccctcctctt atttgggcgt gtcgtctatc | 720 |
| aatgctgttc tcaaagtgat tctctgcctt gaccctggcg ccctctctta cttctctcat | 780 |
| ccctcgacca acacagactc cagggactca gctctaggat actccccagc agaagcacaa | 840 |
| ccatggccgg tccaagagtc tcagcaacca ataacgcccc ctcaaccaca tcgaccagta | 900 |
| acagagatgc agttgctcga cgcctacttt acttattttc agccattcgt gcccatgcta | 960 |
| gatgaggaag ttttccgcga ggtctatcac tcggggtgta gaaaggatga acgttggctg | 1020 |
| gcactgctga acattgtgct tgccttgggt agcatcgcag catgtccatc ggatgacatg | 1080 |
| tcccacacaa tttacgccca gcgctgtaag agctacttga atttagaatc gcttggatcc | 1140 |
| tcacatatag agaccatcca gactctcggc cttctgggag gcagtatcct tcattatgtc | 1200 |
| agtcaaccca atctggcata ttcgctcatg ggagctgcgc tgcgcatggc tgcagctttg | 1260 |
| ggcttgcaca aagagttttc agataaccag gaagggtcgt gtaagcagaa catatattcg | 1320 |

```
actgacctga aacggcgagt gtggtggtcg ctgttttgct tggacacttg gggctgtatg    1380
actctggggc gaccgagtat gggacgattt ggaccgacga ttaccgttaa actgccgcag    1440
taccgagaaa gagtatgtat gcgtccgaac tttgtgattc tgtcattcta acccttccag    1500
gggaatgttc tcgacattat accgcttcta gaaaacgttc ggttctgcaa aattgcgaca    1560
cagatccagg aaattctggc tgccgctccg ttgacgaggt accacgagat gtcgcacttt    1620
gataatcaac tgttagagtg gtatgagaac cttccgtata tactcaaaga ccacgagcca    1680
tgctccgaat caattatcat caccaggaca gtcatgaaat ggcggtacta aaccagcgt    1740 atgctcatat accgtccaac tctactcagc tacgccatgc ggcgggttcc atatattgct    1800
ctccgttccg aagagcggac ggcgatcgaa aggtgtcgac agatcgcgga ggctacaatt    1860
caagacattt cttcaacggc ccagtcacat caaatgtcgg gctggagtgc agtctggctc    1920
atattccagg cagtcatggt tccctattg ggattgtttc tcaacgacaa cacaacgagt    1980
gaccctagag ctactgttgc gagctgccaa tctcaagttg agatggctat gcttgtcctg    2040
gcccgactgg aacaatggag cccgactgca aaaggacgt tgggtgccgt atcgcagata    2100
ttggaagcta gtaagagagg gactaacatg gccaacgagg ctggccttgt caatagcatg    2160
tttgctgtct cacgcgaggg ggcagtgcct cgagccgctt cagggtttca tccgtcccaa    2220 aacatttttcc ttcagaatga ggcaggcttt gatccgtttg cgcctccagt tattgacgac    2280
tcgacggctc agtacctatg ggacttcttg agctggagcg atagcagcct atggcctgga    2340
ataacggaca ccaatagctt caacgacgaa acgctgttcg cccaaacaga caaaaccatg    2400
aaatatccca caacggtgc agcctttatg gggggctcta tgggagacgg tgcctactat    2460
gcaaatccac ctttgcccta ctactaa                                      2487

<210> SEQ ID NO 46
<211> LENGTH: 24
<212> TYPE: DNA
<213> ORGANISM: Artificial Sequence
<220> FEATURE:
<223> OTHER INFORMATION: Primer

<400> SEQUENCE: 46
tgccatctca ggggacctct actg                                            24

<210> SEQ ID NO 47
<211> LENGTH: 24
<212> TYPE: DNA
<213> ORGANISM: Artificial Sequence
<220> FEATURE:
<223> OTHER INFORMATION: Primer

<400> SEQUENCE: 47
ccgcaatatg gtcagtcacg agac                                            24

<210> SEQ ID NO 48
<211> LENGTH: 26
<212> TYPE: DNA
<213> ORGANISM: Artificial Sequence
<220> FEATURE:
<223> OTHER INFORMATION: Primer

<400> SEQUENCE: 48
actcctttgt caatgacatc ttcgag                                          26

<210> SEQ ID NO 49
```

```
<211> LENGTH: 25
<212> TYPE: DNA
<213> ORGANISM: Artificial Sequence
<220> FEATURE:
<223> OTHER INFORMATION: Primer

<400> SEQUENCE: 49
attcacctgg caggataagt ctgac                                              25

<210> SEQ ID NO 50
<211> LENGTH: 40
<212> TYPE: PRT
<213> ORGANISM: Aspergillus oryzae

<400> SEQUENCE: 50

Thr Leu Arg Ala Cys Thr Ser Cys Arg His Arg Lys Ile Lys Cys Asp
1               5                   10                  15

Gly Glu Lys Pro Cys Glu Ala Cys Arg Trp Tyr Lys Lys Ala Asp Gln
            20                  25                  30

Cys His Tyr Ala Asp Pro Arg Pro
        35                  40

<210> SEQ ID NO 51
<211> LENGTH: 99
<212> TYPE: PRT
<213> ORGANISM: Aspergillus oryzae

<400> SEQUENCE: 51

His Ile Glu Thr Ile Gln Thr Leu Gly Leu Leu Gly Gly Gln Tyr Leu
1               5                   10                  15

His Tyr Val Ser Gln Pro Asn Leu Ala Tyr Ser Leu Met Gly Ala Ala
            20                  25                  30

Leu Thr Met Ala Ala Ala Leu Gly Leu His Lys Glu Phe Ser Asp Asn
        35                  40                  45

Gln Glu Gly Ser Cys Lys Gln Asn Ile Tyr Ser Thr Asp Leu Lys Arg
    50                  55                  60

Arg Val Trp Trp Ser Leu Phe Cys Leu Asp Thr Trp Gly Cys Met Thr
65                  70                  75                  80

Leu Gly Arg Pro Ser Met Gly Arg Phe Gly Pro Thr Ile Thr Val Lys
                85                  90                  95

Leu Pro Gln
```

TRANSCRIPTION REGULATORY FACTORS FOR MANNANASES OR CELLULASES, AND GENES FOR THE TRANSCRIPTION REGULATORY FACTOR

FIELD OF INVENTION

The present invention relates to a transcription regulatory (controlling) factor for mannan hydrolases or cellulose hydrolases, a gene encoding the transcription regulatory factor, a recombinant vector including the gene, a transformant transformed with the vector, and methods of producing the transcription regulatory factor, the mannan hydrolases, and the cellulose hydrolases using the transformant.

BACKGROUND OF THE INVENTION

β-Mannans such as glucomannan and galactomannan are compounds having 1,4-β-D-mannoside bond and are widely present in the natural world as a component of hemicellulose, which is one of main components of plant cell walls. This 1,4-β-D-mannoside bond is hydrolyzed by β-1,4-mannanase (EC3.2.1.78) or β-mannosidase (EC3.2.1.25). α-1,6-galactoside bond present in galactomannan is hydrolyzed by α-galactosidase (EC3.2.1.22). Acetylated β-mannans are deacetylated by the action of acetylmannan esterase (EC3.1.1.6) (throughout this specification, β-1,4-mannanase, β-mannosidase, α-galactosidase, and acetylmannan esterase are collectively referred to as "mannan hydrolases"). Among these mannan hydrolases, β-1,4-mannanase is an industrially useful enzyme and is widely used in industries such as foods, stockbreeding, and papermaking (throughout this specification, β-1,4-mannanase is referred to as "mannanase", and β-1,4-mannosidase is referred to as "mannosidase").

As the mannanases, there are known those derived from Ascomycotina filamentous fungi such as *Trichoderma reesei* (for example, see NPL 1) and *Aspergillus aculeatus* (for example, see PTL 1) and those derived from Basidiomycotina filamentous fungi such as *Agaricus bisporus* (for example, see NPL 2). As the mannanases derived from bacteria (for example, see NPL 3), there are known those derived from, for example, *Streptomyces lividans* (for example, see NPL 4) and *Pseudomonas fluorescens* (for example, see NPL 5). Genes of these mannanases have been also reported.

As enzymes that are known but their genes have not been reported, there are known, for example, those derived from *Aspergillus tamarii* (for example, see NPL 6) and *Penicillium multi. color* (for example, see PTL 2).

*Aspergillus oryzae* and *Aspergillus sojae*, which are yellow koji molds, have been used in production of brewed foods such as soy sauce, miso, and rice wine from ancient times in Japan. These koji molds have high enzyme-producing abilities and high safety credibility based on the longtime use thereof and are therefore industrially important microorganisms. Regarding these yellow koji molds, there are reports on mannanase derived from *Aspergillus oryzae* (for example, see NPL 7) and also reports on the enzyme after purification and a gene of the enzyme (for example, see PTL 3).

As one of transcription regulatory factors that positively or negatively regulate the expression of genes of the above-mentioned mannanases, in prokaryotes, a negative regulatory factor (reppressor) derived from *Bacillus subtilis* has been reported (for example, see NPL 8.). However, in eukaryotes including molds, transcription regulatory factors for mannanases have not been found yet. In eukaryotes, not only transcription regulatory factors regulating the expression of genes of mannanases, but also transcription regulatory factors regulating the expression of genes of mannosidase and α-galactosidase, which participate in hydrolysis of mannans, have not been found. Therefore, production of a eukaryotic microorganism strain, the mannan hydrolase-producing capability of which has been enhanced by forced expression of the transcription regulatory factor, has not also been investigated.

In degradation of woody biomass, in addition to mannan hydrolases, the actions of cellulose hydrolases (e.g., a cellulase, cellobiohydrolases, or β-glucanases, or β-glucosidase that degrades oligosaccharides produced by the action of a cellobiohydrolase or a glucanase) are also important. Accordingly, it is expected that production of a large amount of cellulose hydrolases together with mannan hydrolases is effective for efficient production of enzyme preparations of degrading woody biomass. If the transcription regulatory factor positively regulates the expression of genes of both mannan hydrolase and cellulose hydrolase, it is probably possible to breed a eukaryotic microorganism strain of which capability of producing both the hydrolases has been enhanced by forced expression of the transcription regulatory factor. However, such investigation has not been performed to date.

CITATION LIST

Patent Literature

Patent Literature 1: U.S. Pat. No. 5,795,764
Patent Literature 2: Japanese Patent Laid-Open No. 2001-145485
Patent Literature 3: Japanese Patent Laid-Open No. 2003-164286

Non-Patent Literature

Non-Patent Literature 1: Appl Environ Microbiol., 61 (3): 1090-7, 1995
Non-Patent Literature 2: Appl Environ Microbiol., 67 (5): 2298-303, 2001
Non-Patent Literature 3: Biochim Biophys Acta., 1243 (3): 552-4, 1995
Non-Patent Literature 4: Biochem. J., 290 (Pt 3): 857-63, 1993
Non-Patent Literature 5: Biochem. J., 305 (Pt 3): 1005-1010, 1995
Non-Patent Literature 6: Biochem. J., 219 (3): 857-863, 1984
Non-Patent Literature 7: Cytobios, 105 (409): 115-30, 2001
Non-Patent Literature 8: FEMS Microbiol Lett, 279: 103-109, 2008

SUMMARY

Problems to be Solved by the Invention

It is an object of the present invention to provide a novel transcription regulatory factor that regulates transcription/expression of genes of mannan hydrolases or cellulose hydrolases, a novel gene encoding the transcription regulatory factor, a recombinant vector including the gene, a transformant transformed with the vector, and methods of efficiently producing the transcription regulatory factor, the mannan hydrolases, and the cellulose hydrolases using the transformant.

Means for Solving the Problems

The present inventors have conducted intensive studies for solving the above-mentioned problems and have succeeded in cloning of a protein having a capability of regulating the transcription of expression of a gene of mannan hydrolases or cellulose hydrolases in a yellow koji mold, *Aspergillus oryzae* (throughout the specification, the protein may be also simply referred to as "transcription regulatory factor" hereinafter). As a result, the present invention has been completed. That is, the present invention relates to the following aspects.

1) A protein:
   (a) comprising an amino acid sequence represented by SEQ ID NO: 2;
   (b) comprising the amino acid sequence represented by SEQ ID NO: 2 wherein one or several amino acids are deleted, substituted or added, and having a regulating capability of the transcription of genes for mannan hydrolases or cellulose hydrolases; or
   (c) comprising an amino acid sequence having 70% or more identity with the amino acid sequence represented by SEQ ID NO: 2 or its partial fragment, and having a regulating capability of the transcription of genes for mannan hydrolases or cellulose hydrolases.

2) A gene encoding a protein:
   (a) comprising an amino acid sequence represented by SEQ ID NO: 2;
   (b) comprising the amino acid sequence represented by SEQ ID NO: 2 wherein one or several amino acids are deleted, substituted or added and having a regulating capability of the transcription of genes for mannan hydrolases or cellulose hydrolases; or
   (c) comprising an amino acid sequence having 70% or more identity with the amino acid sequence represented by SEQ ID NO: 2 or its partial fragment, and having a regulating capability of the transcription of genes for mannan hydrolases or cellulose hydrolases.

3) A gene consisting of aDNA:
   (a) comprising a base sequence represented by SEQ ID NO: 1;
   (b) hybridizing under stringent conditions with polynucleotides comprising the base sequence represented by SEQ ID NO: 1 or a base sequence complementary to said base sequence, and encoding the protein having a regulating capability of the transcription of genes for mannan hydrolases or cellulose hydrolases;
   (c) hybridizing under stringent conditions with polynucleotides encoding the amino acid sequence represented by SEQ ID NO: 2 or with polynucleotides complementary to said polynucleotides, and encoding the protein having a regulating capability of the transcription of genes for mannan hydrolases or cellulose hydrolases; or
   (d) having 70% or more identity with the DNA of the base sequence represented by SEQ ID NO: 1, and encoding the protein having a regulating capability of the transcription of genes for mannan hydrolases or cellulose hydrolases.

4) A recombinant vector comprising the gene.

5) A transformant comprising the recombinant vector.

6) A method for the production of transcription regulatory factors, comprising culturing the transformant and recovering said transcription regulatory factors from the resulting culture product.

7) A method for the production of mannan hydrolases or cellulose hydrolases, comprising culturing the transformant and recovering said mannan hydrolases or cellulose hydrolases from the resulting culture product.

8) A method for increasing the production of mannan hydrolases or cellulose hydrolases by the transformant, comprising culturing said transformant.

BRIEF DESCRIPTION OF THE DRAWINGS

FIG. 1 shows the confirmation results of restoration of pyrG of the RkuptrP2-1ΔAF/P strain by PCR.

FIG. 2 shows the confirmation results of restoration of pyrG of the RkuptrP2-1ΔAF/P strain by Southern hybridization.

FIG. 8 roughly shows the results of DNA microarray analysis of a manR disruptant.

FIG. 9 shows the top 25 genes among the genes that exhibited a reduction in expression thereof in the DNA microarray analysis of the manR disruptant.

FIG. 20 shows the results of a halo assay of extracellular cellulase activity in a koji mold manR disruptant and a forced expression strain.

FIG. 21 shows influence (array analysis results) of manR disruption and forced expression in culture using microcrystalline cellulose (Avicel) as a carbon source.

FIG. 22 shows influence (array analysis results) of manR disruption and forced expression in culture using wheat bran as a carbon source.

DISCLOSURE OF INVENTION

Advantages of the Invention

Figure 3:
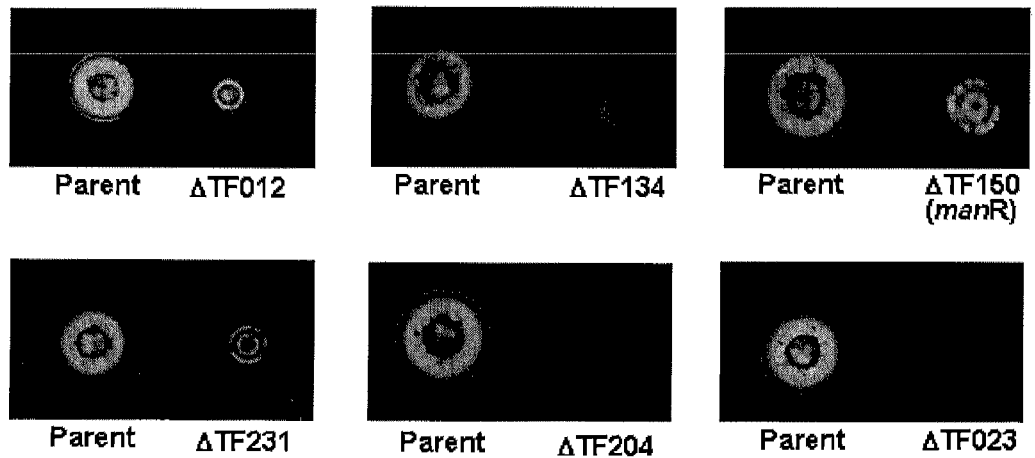
FIG. 3 shows disruptants exhibited changes in activity in screening.

The present invention can provide a novel transcription regulatory factor for mannan hydrolases or cellulose hydrolases, a gene encoding the transcription regulatory factor, and a recombinant vector and a transformant including the gene. In addition, the present invention provides a method of producing the transcription regulatory factor and can further provide a method of enhancing the production of mannan hydrolases or cellulose hydrolases. As a result, it is possible to efficiently produce the mannan hydrolases or the cellulose hydrolases in a koji mold. In addition, the transcription regulatory factor can be improved through protein engineering, which allows improvement of eukaryotic microorganisms that are used in production of enzymes for food processing or in production of brewed foods.

Embodiments of the Invention

The transcription regulatory factor of the present invention is a protein including an amino acid sequence represented by SEQ ID NO: 2. The transcription regulatory factor can be obtained from, for example, a homogenate solution of a yellow koji mold such as *Aspergillus oryzae*. Alternatively, the transcription regulatory factor can be obtained by expressing a transcription regulatory factor gene cloned from, for example, the yellow koji mold in an appropriate host-vector system.

The transcription regulatory factor may have deletion, substitution, or addition of one or several (e.g., one to five) amino acids in the amino acid sequence represented by SEQ ID NO: 2, as long as the factor has a capability of regulating transcription. Furthermore, the transcription regulatory factor may be a protein including an amino acid sequence having 70% or more, preferably 80% or more, more preferably 85% or more, and most preferably 90% or more identity with the amino acid sequence represented by SEQ ID NO: 2 or its partial fragment, as long as the factor has a capability of regulating transcription.

In order to determine the sequence identity in two amino acid sequences or base sequences, the sequences are pre-treated to relatively optimum states. For example, one sequence is provided with a gap and is thereby optimized in alignment with the other sequence. Then, the amino acid residue or base at each site is compared. In the case that a first sequence has the same amino acid residue or base as that at the corresponding site of a second sequence, the sequences are identical to each other at the site. The sequence identity in two sequences is shown by a percentage of the number of sites that are identical between the sequences to the total number of sites (total number of amino acids or bases).

In accordance with the above-described principle, the sequence identity in two amino acid sequences or base sequences is determined by the Karlin-Altschul algorithm (Proc. Natl. Acad. Sci. USA, 87: 2264-2268, 1990 and Proc. Natl. Acad. Sci. USA, 90: 5873-5877, 1993). A BLAST program using such an algorithm was developed by Altschul, et al. (J. Mol. Biol., 215: 403-410, 1990). The Gapped BLAST is a program for determining sequence identity with a higher sensitivity than that of the BLAST (Nucleic Acids Res., 25: 3389-3402, 1997). These programs are mainly used for searching databases for a sequence showing high sequence identity with a query sequence. These programs can be used by, for example, accessing to a website of U.S. National Center for Biotechnology Information on the Internet.

As the sequence identity between sequences, a value determined using BLAST 2 Sequences software (FEMS Microbiol Lett., 174: 247-250, 1999) developed by Tatiana A. Tatusova, et al. is used. This software can be used by accessing to a website of U.S. National Center for Biotechnology Information on the Internet and also can be obtained. The programs and parameters that are used are as follows. In the case of an amino acid sequence, a Blastp program is used with parameters; Open gap: 11 and extension gap: 1 penalties, gap x_drop off: 50, expect: 10, word size: 3, and Filter: ON. In the case of a base sequence, a Blastn program is used with parameters; Reward for a match: 1, Penalty for a mismatch: −2, Strand option: Both strands, Open gap: 5 and extension gap: 2 penalties, gap x_drop off: 50, expect: 10, word size: 11, and Filter: ON. These parameters are used as default values on the websites.

If no sequence showing significant identity with a query sequence has been found in the BLAST software, FASTA software (W. R. Pearson and D. J. Lipman, Proc. Natl. Acad. Sci. USA, 85: 2444-2448, 1988) having higher sensitivity may be used for searching a sequence showing sequence identity in databases. The FASTA software can be used by, for example, accessing to a website of GenomeNet. In also this case, default values are used as parameters. For example, in the case of searching a base sequence, nr-nt is used as the database with a ktup value of 6. In any of these cases, when an overlap of 30% or more, 50% or more, or 70% or more to the total is not shown, a functional relationship is not necessarily estimated. Therefore, the percentage is not used as a value showing the sequence identity between two sequences.

The transcription regulatory factor gene of the present invention can be obtained from, for example, yellow koji molds such as *Aspergillus sojae* and *Aspergillus oryzae*, other filamentous fungi, or other fungi. More specific examples thereof include *Aspergillus oryzae* RIB40 strain (Deposition Organization: National Research Institute of Brewing, Deposit ID NO: RIB40). These cells are cultured in a medium under conditions for inducing production of mannan hydrolases, and the total RNA is collected by a common method. As the medium, for example, a Czapek-Dox minimal medium containing 1% glucomannan as a carbon source can be used. After shaking culture in the medium for an appropriate period, for example, for 20 hours, the cells are collected and an appropriate amount, for example, 0.3 g thereof is pulverized in a mortar filled with liquid nitrogen using a pestle, and the total RNA is prepared by a method of Cathala, et al. (DNA, 2: 329-335, 1983).

The thus-obtained total RNA is used as a template for RT-PCR. The primers may be any combination that can amplify the transcription regulatory factor gene of the present invention. For example, oligonucleotides represented by SEQ ID NOs: 35 and 36 described below can be used.

The RT-PCR can be performed by a common method using a commercially available kit, for example, PrimeScript RT-PCR kit (manufactured by Takara Bio).

The obtained DNA containing the mannanase gene of the present invention can be incorporated into a plasmid by a common method, for example.

The base sequence of the thus-obtained DNA can be determined by a Sanger method using a commercially available reagent and a DNA sequencer. The resulting DNA containing the transcription regulatory factor gene of the present invention and an example of the transcription regulatory factor encoded thereby are shown in SEQ ID NOs: 1 and 2, respectively.

The transcription regulatory factor gene may be a gene encoding a protein having deletion, substitution, or addition of one or several (e.g., one to five) amino acids in the amino acid sequence represented by SEQ ID NO: 2, as long as the factor has the capability of regulating the transcription of genes for mannan hydrolases or cellulose hydrolases. These genes can be obtained by various known mutation-introducing methods, as well as selection by hybridization described below.

The transcription regulatory factor gene can be also obtained by a selection method through hybridization. Examples of the gene source include yellow koji molds such as *Aspergillus sojae* and *Aspergillus oryzae*. RNA or genomic DNA is prepared from these organisms by a common method and is incorporated into a plasmid or phage to prepare a library.

Subsequently, a nucleic acid used as a probe is labeled by a method appropriate for the detection method. The nucleic acid used as a probe may be any nucleic acid having a length for obtaining a sufficient specificity. For example, a nucleic acid containing at least 100 bases or more, preferably 200 bases or more, and most preferably 450 bases or more of the sequence represented by SEQ ID NO: 1 or the entire sequence represented by SEQ ID NO: 1.

Then, a clone that hybridizes to the labeled probe under stringent conditions is selected from the library. The hybridization can be performed by colony hybridization in the case of a plasmid library and can be performed by plaque hybridization in the case of a phage library.

The stringent conditions are conditions that allow clear distinguishing of the signal of specific hybridization from the signal of non-specific hybridization and vary depending on the hybridization system used and the kind, sequence, and length of the probe. The conditions can be determined by changing the temperature of hybridization and changing the temperature and salt concentration of washing. For example, if the signal of non-specific hybridization is also strong, the specificity can be increased by raising the temperatures for the hybridization and washing and optionally decreasing the salt concentration for washing.

In contrast, if the signal of specific hybridization also is not detected, the hybridization can be stabilized by decreasing the temperatures for hybridization and washing and optionally increasing the salt concentration for washing. Such optimization can be easily performed by researchers in this technical field.

In a specific example of the stringent conditions, hybridization is performed overnight (about 8 to 16 hr) using 5×SSC, a 1.0% (W/V) nucleic acid hybridization blocking reagent (manufactured by Roche Diagnostics), 0.1% (W/V) N-lauroyl sarcosine, and 0.02% (W/V) SDS; and washing is performed for 15 min twice using 0.5×SSC and 0.1% (W/V) SDS, preferably 0.1×SSC and 0.1% (W/V) SDS. The temperature for the hybridization and the washing is 52° C. or higher, preferably 57° C. or higher, more preferably 62° C. or higher, and most preferably 67° C. or higher.

A base sequence having 70% or more, preferably 80% or more, more preferably 85% or more, and most preferably 90% or more identity with the base sequence represented by SEQ ID NO: 1 is expected to encode a protein having substantially the same activity as that of the transcription regulatory factor of the present invention. Such a DNA can be obtained using the above-described hybridization as a parameter or also can be easily found from DNAs of which functions are unknown, obtained by, for example, genome base sequence analysis, or public databases by searching using, for example, the above-mentioned BLAST software. Such a search is a method that is usually used by researchers in this technical field.

The obtained DNA encodes a protein having the capability of regulating the transcription of mannan hydrolases or cellulose hydrolases. This can be confirmed, as described below, by disrupting the target gene in an appropriate host and culturing the disruptant on a minimal medium containing glucomannan as a single carbon source to confirm disappearance or a significant reduction in mannanase activity of the disruptant; or by forcing the target gene expression in an appropriate host and culturing the strain forced to express the gene on a minimal medium containing carboxymethyl cellulose as a single carbon source to confirm disappearance or a significant increase in cellulase activity.

The recombinant vector of the present invention can be obtained by linking the transcription regulatory factor gene to an appropriate vector. Any vector that allows production of the transcription regulatory factor in a host for transformation can be used. For example, plasmids, cosmids, phages, viruses, and vectors such as chromosome integration vectors and artificial chromosome vectors can be used.

The vector may contain a marker gene for enabling selection of transformed cells.

Examples of the marker gene include genes complementing the auxotrophy of a host, such as ura3 and nIaD, and genes resistant to drugs such as ampicillin, kanamycin, and oligomycin.

It is desirable that the recombinant vector contain a promoter that can express the gene of the present invention in a host cell or contain another regulatory sequence such as an enhancer sequence, a terminator sequence, or a polyadenylated sequence.

Examples of the promoter include a GAL1 promoter, a TEF1 promoter, and a lac promoter. In addition, the promoter may be provided with a tag for purification. Specifically, purification using a nickel column is possible by linking an appropriate linker sequence to the downstream of the transcription regulatory factor gene and linking six or more codons of base sequence encoding histidine.

The transformant of the present invention can be obtained by transforming a host with a recombinant vector. Any host that can produce the transcription regulatory factor can be used without particular limitation. For example, yeasts such as *Saccharomyces cerevisiae* and *Zygosaccharomyces rouxii*, filamentous fungi such as *Aspergillus sojae, Aspergillus oryzae*, and *Aspergillus niger*, and bacteria such as *Escherichia coli* and *Bacillus subtilis* can be used. Furthermore, a forced expression strain can be produced by using a constitutive promoter such as a TEF1 promoter, and it is possible to forcibly express the protein to be regulated by this forced expression strain.

The transformation can be perfolined by a known method appropriate for the host. In the case of using a yeast as the host, for example, a method using lithium acetate, described in Methods Mol. Cell. Biol., 5, 255-269 (1995), can be employed. In the case of using a filamentous fungus, for example, a method using polyethylene glycol and calcium chloride after protoplastation, described in Mol. Gen. Genet., 218: 99-104, 1989, can be employed. In the case of using a bacterium as the host, for example, a method by electroporation, described in Methods Enzymol., 194: 182-187, 1990, can be employed.

The method of producing the transcription regulatory factor of the present invention includes culturing a transformant expressing the transcription regulatory factor and efficiently collecting the transcription regulatory factor protein from the obtained culture product by a common method. The medium and the culture method are appropriately selected depending on the type of the host and the expression regulatory sequence in the recombinant vector. For example, in the case of using *Saccharomyces cerevisiae* as the host and a GAL1 promoter as the expression regulatory sequence, the transcription regulatory factor of the present invention can be produced by pre-culturing the cells in a minimal liquid medium containing raffinose as a carbon source and diluting, inoculating, and culturing the pre-cultured cells in a minimal liquid medium containing galactose and raffinose as a carbon source.

In the case of using *Aspergillus sojae* as the host and a amyB promoter as the expression regulatory sequence, for example, the transcription regulatory factor can be highly expressed by culturing the cells in a minimal liquid medium containing maltose as a carbon source. In the case of using *Escherichia coli* as the host and a lac promoter as the expression regulatory sequence, for example, the transcription regulatory factor can be produced by culturing the cells in a liquid medium containing IPTG. In the case of that the transcription regulatory factor is produced insides or on the surfaces of cells, the transcription regulatory factor can be obtained by separating the cells from the medium and appropriately treating the cells. For example, in the case of the protein is produced on the surfaces of *Saccharomyces* cerev siae cells, the cells are pulverized, treated with a low concentration of a nonionic surfactant, such as Triton X-100, Tween-20, or Nonidet P-40, and subjected to centrifugation to collect the transcription regulatory factor from the supernatant. In the case of producing the transcription regulatory factor in a culture medium, the transcription regulatory factor can be obtained by removing the cells by, for example, centrifugation and filtration. In any of these cases, a transcription regulatory factor having a higher degree of purity can be obtained by subjecting the obtained transcription regulatory factor to a common purification method, such as ammonium sulfate fractionation, various chromatographies, alcohol precipitation, or ultrafiltration.

The transcription regulatory factor of the present invention positively regulates the expression of mannan hydrolases or cellulose hydrolases. Therefore, if the mannan hydrolases or the cellulose hydrolases of a species used as the host are regulated by the transcription regulatory factor, the production of the mannan hydrolases or the cellulose hydrolases is enhanced by forcibly expressing the transcription regulatory factor, and thereby the enzyme groups can be efficiently produced.

Any species, the expression of mannan hydrolase genes of which is regulated by the transcription regulatory factor, can be used as the host without particular limitation, and specific examples thereof include *Aspergillus oryzae* and *Aspergillus niger*. The medium and the culture method can be appropriately selected depending on the type of the host and the expression regulatory sequence in the recombinant vector.

For example, in the case of using *Aspergillus oryzae* as the host and a TEF1 promoter as the expression regulatory sequence, the mannan hydrolases or the cellulose hydrolases can be efficiently produced by solid culture of a transformant highly expressing the transcription regulatory factor using, for example, wheat bran.

In the case of that mannan hydrolases or cellulose hydrolases are produced insides or on the surfaces of cells by forced expression of the transcription regulatory factor, they can be obtained by separating the cells from the medium and appropriately treating the cells.

For example, in the case of the hydrolases are produced on the surfaces of *Aspergillus oryzae* cells, the cells themselves can be used as an enzyme preparation, but the mannan hydrolases or the cellulose hydrolases may be collected by pulverizing the cells and then subjecting the pulverized cells to treatment with a low concentration of a nonionic surfactant, such as Triton X-100, Tween-20, or Nonidet P-40, and centrifugation to collect the supernatant.

In the case of producing the mannan hydrolases or the cellulose hydrolases in a culture medium, the mannan hydrolases or the cellulose hydrolases can be obtained by removing the cells by, for example, centrifugation and filtration. In any of these cases, mannan hydrolases having higher degrees of purity can be obtained by subjecting the obtained hydrolases to a common purification method, such as ammonium sulfate fractionation, various chromatographies, alcohol precipitation, or ultrafiltration.

The presence or absence of the extracellular mannanase activity can be tested by the following method. A sample to be tested is inoculated to a plate of a Czapek-Dox minimal medium (0.05% KCl, 0.2% NaNO3, 0.1% KH2PO4, 0.05% MgSO4, 0.001% FeSO4, and 2.0% agar) containing 1.0% glucomannan (manufactured by Megazyme) and is cultured at 30° C. for about 2 to 4 days. The number of culture days and the culture temperature should be appropriately adjusted depending on the sample. After completion of the culture, about 8 mL of 0.25% Congo red is added to the plate for staining for 15 min, followed by washing the plate with about 8 mL of a 1.0 M NaCl solution for 30 min three times. After completion of the washing, about 3 to 5 mL of 5.0% acetic acid is added to the plate, and the plate is left at room temperature for about 10 min to change the color of the Congo red to blue to detect halo formed by the extracellular mannanase activity.

The activity of exctracellular cellulose hydrolase can be tested by the following method. A sample to be tested is inoculated to a plate of a Czapek-Dox minimal medium (0.05% KCl, 0.2% NaNO3, 0.1% KH2PO4, 0.05% MgSO4, 0.001% FeSO4, and 2.0% agar) containing 2.0% carboxymethyl cellulose (manufactured by Sigma-Aldrich) as a single carbon source and is cultured at 30° C. for about 3 to 4 days. The number of culture days and the culture temperature should be appropriately adjusted depending on the sample. After completion of the culture, as in the test of the extracellular mannanase activity described above, the activity of the extracellular cellulase can be tested through staining with Congo red and detection of the halo.

The present invention will be specifically described according to examples below, but the technical scope of the present invention should not be restricted by these descriptions in any manner.

Example 1

Screening of Transcription Regulatory Factor (manR) of Koji Mold

The genome sequence of a koji mold, an *Aspergillus oryzae* RIB40 strain, was determined in 2005 (Nature, 438: 1157, 2005), and the information thereon is available from DOGAN database (http://www.bio.nite.go.jp/dogan/MicroTop?GENOME_ID=ao). Before, the present inventors manually annotated the transcription regulatory factor gene based on this genome information and produced a library of transcription regulatory factor gene disruptants, the genes of which are comprehensively disrupted (5th International *Aspergillus* Meeting, No. 16, 2008, Edinburgh, UK).

The microorganism strains used in the production of the library of the transcription regulatory factor gene disruptants are an *Aspergillus oryzae* RkuN16ptr1 strain (Mol. Genet. Genomics, 275: 460, 2006; Biosci. Biotechnol. Biochem, 70: 135, 2006) and its derivative, *Aspergillus oryzae* RkuptrP2-1 5-FOA-resistant strain No. 2 (Appl. Environ Microbiol., 74: 7684, 2008). Both of these two types of strains are derivatives of an *Aspergillus oryzae* RIB40 strain, the genome sequence of which has been completed.

Throughout the specification, *Aspergillus oryzae* RkuptrP2-1 5-FOA-resistant strain No. 2 is referred to as RkuptrP2-1ΔAF strain or host strain. In the RkuN16ptr1 strain, in order to improve the efficiency of gene targeting, Ku70, which is a gene involving in non-homologous recombination, is disrupted (Mol. Genet. Genomics, 275: 460, 2006), and in order to enable selection based on auxotrophy, the pyrG gene is disrupted to obtain an uridine auxotrophic strain. Furthermore, in the RkuptrP2-1ΔAF strain, the aflatoxin biosynthesis cluster of the RkuN16ptr1 strain is removed to avoid unexpected production of aflatoxin (Appl. Environ. Microbiol., 74: 7684, 2008). Excluding the mutation sites described above, these two strains have the same sequence as that of a wild-type strain, *Aspergillus oryzae* RIB40. A koji mold mannanase transcription regulatory factor disruptant (TF150 disruptant, i.e., manR disruptant) described below is produced using the RkuptrP2-1ΔAF strain as a host. Hereinafter, the *Aspergillus oryzae* RIB40 strain is referred to as wild-type strain. For the purpose of finding a transcription regulatory factor from the disruptant library, the present inventors have conducted screening of the disruptant library by a halo assay for mannanase activity.

The disruptants of the library were obtained by pyrG-positive selection. Therefore, all the disruptants are pyrG+ strains, and it is not adequate to use the host strain, which is a pyrG deficient strain, as a control in the screening for a transcription regulatory factor using a produced disruptant. Accordingly, a strain where the pyrG gene of the host strain has been restored was produced and was used as a control. The strain was produced by the following method. Incidentally, the method of producing this host strain is also described in Fungal Genetics and Biology, 47, 10-18, 2010.

A DNA fragment of about 4.1 kb including a structural gene of the pyrG gene of the wild-type strain, a promoter, and a terminator was amplified by PCR using the oligonucleotide primers represented by SEQ ID NOs: 3 and 4.

TABLE 1

| No. | Sequence |
|---|---|
| SEQ ID NO: 3 | ACGTGTGCAGGTCTCGGACAAAACAC |
| SEQ ID NO: 4 | CCTCCCGCCTCTATCGACAAATAATATG |

KOD plus (manufactured by TOYOBO), which has high accuracy, was used as the enzyme, and 150 ng of a genomic DNA derived from the wild-type strain was used as the template DNA. The reaction system was conducted at a total amount of 300 μL. The final concentration of MgSO$_4$ in the reaction solution was adjusted to 1.2 mM, and dimethyl sulfoxide (manufactured by Sigma-Aldrich Japan) was added to the reaction solution at a final concentration of 5.0%. The PCR reaction was performed at 94° C. for 2 min and then 30 cycles of three steps consisting of 94° C. for 10 sec, 55° C. for 15 sec, and 68° C. for 5 min. A part of the amplification product was subjected to electrophoresis on a 0.8% agarose gel to confirm the amplification of the DNA fragment of about 4.1 kb. After the confirmation of the amplification by the PCR reaction, all of the remaining reaction solution was subjected to electrophoresis on a 0.8% agarose gel to purify the DNA fragment by the gel extraction. Then, the purified DNA fragment was concentrated by alcohol precipitation and was used as a vector for restoration of pyrG.

This vector was introduced into the above-mentioned host strain by a common method, i.e., a protoplast-PEG method (Gene, 61: 385, 1987).

The selection of transformants was performed by pyrG positive selection using a Czapek-Dox minimal medium containing 1.2 M sorbitol, but not containing uridine.

Preparation of Genomic DNA from Transformant

In order to conduct an experiment of confirming restoration of the pyrG gene of the transformant, a genomic DNA from each sample was prepared. The transformant, the host strain, and the wild-type strain were each inoculated to 40 mL of a dextrin-peptone medium in a 150-mL Erlenmeyer flask and were cultured at 30° C. for three days at 150 rpm.

In the case of culture of the host strain, the medium was supplemented with filtration-sterilized uridine at a final concentration of 15 mM. After completion of the culture, the cells were collected by filtration, dried by absorbing moisture with a paper towel, and were frozen rapidly using liquid nitrogen.

Subsequently, the frozen cells were placed in a mortar cooled in advance by pouring liquid nitrogen and were absolutely pulverized with a pestle cooled in advance with liquid nitrogen. The total DNA was extracted from the pulverized cells using a Genomic DNA extraction kit (manufactured by Promega) and was treated with DNase-free RNase I (manufactured by Nippon Gene) to degrade contaminated RNA. The resulting sample was used in the subsequent experiments.

Confirmation of pyrG Restored Strain by PCR

Whether the pyrG gene in a transformant was restored was investigated by PCR using about 150 ng of genomic DNA of the transformant prepared by the above-described method as the template and oligonucleotide primers represented by SEQ ID NOs: 3 and 4. As the control, a reaction system using the genomic DNAs derived from the host strain and the wild-type strain as templates was employed. ExTaq (manufactured by Takara Bio) was used as the enzyme for PCR, and dimethyl sulfoxide (manufactured by Sigma-Aldrich Japan) was added to the reaction solution at a final concentration of 5.0%. Other conditions were adjusted to those described in the manual attached to the enzyme, and the total amount of the reaction solution was adjusted to 20 μL. The PCR reaction was performed at 94° C. for 2 min and then 30 shuttle cycles of 94° C. for 10 sec and 68° C. for 5 min. The results are shown in FIG. 1.

The transformant, the host strain, and the wild-type strain were each detected as a single band. The band of the host strain was observed at about 2.8 kb, but the bands of the transformant and the wild-type strain were observed at about 4.1 kb. This suggested that the pyrG gene of the transformant was restored to the same state as that of the wild-type strain and also that the nucleus was purified.

Confirmation of pyrG Restored Strain by Southern Hybridization

Confirmation of the transformant by Southern hybridization was performed. About 5.0 μg of the genomic DNA of each of the transformant, the host strain, and the wild-type strain was digested by restriction enzyme BglII at 37° C. overnight and was then subjected to electrophoresis on a 0.8% agarose gel. The electrophoresed nucleic acids were blotted onto a positively charged nylon membrane, Hybond-N+ (manufactured by GE Healthcare Biosciences), and were subjected to hybridization using a digoxigenin (DIG)-labeled probe at 42° C. overnight. The DIG-labeled probe was produced using a DIG PCR Labeling Kit (manufactured by Roche Diagnostics); ExTaq (manufactured by Takara Bio) was used as the enzyme for PCR; and 150 ng of the genomic DNA of the wild-type strain was used as the template. The oligonucleotide primers represented by SEQ ID NOs: 5 and 6 were used as the PCR primers, and the total amount of the reaction system was adjusted to 25 μL.

TABLE 2

| No. | Sequence |
|---|---|
| SEQ ID NO: 5 | CGTACATTGCCGTGATCAAAACTCAC |
| SEQ ID NO: 6 | GTCACCCTTCGAGGAGAGGTTGACAC |

The washing of the membrane and the detection of signals after the hybridization were performed in accordance with the manual of DIG system (manufactured by Roche Diagnostics). The results are shown in FIG. 2.

In the host strain, since the pyrG gene was deleted, no band was confirmed. In the transformant, a single band was confirmed at about 3 kb, and the size of the band agreed with that of the wild-type strain. Based on these results, it was judged that the pyrG gene of the obtained transformant was restored to the same state as that of the wild-type strain. Furthermore, it was confirmed by PCR that the nucleus of the transformant was purified, and all of the obtained transformants clearly showed phenotype of a pyrG+ strain. Accordingly, it is judged based on these results that the obtained transformant is a pyrG restored strain of the host strain the nucleus of which was purified. This transformant was designated as RkuptrP2-1ΔAF/P strain and was used in subsequent experiments. Throughout the specification, the RkuptrP2-1ΔAF/P strain was referred to as control strain, hereinafter.

Example 2

Method of Screening

Screening of the transcription regulatory factor was performed as follows. A sample to be tested was inoculated to a plate of a Czapek-Dox minimal medium (0.05% KCl, 0.2% NaNO$_3$, 0.1% KH$_2$PO$_4$, 0.05% MgSO$_4$, 0.001% FeSO$_4$, and 2.0% agar) containing 1.0% glucomannan (manufactured by Megazyme) and was cultured at 30° C. for 3 days. After completion of the culture, about 8 mL of 0.25% Congo red was added to the plate for staining for 15 min, followed by washing the plate with about 8 mL of a 1.0 M NaCl solution for 30 min three times. After the washing, about 3 to 5 mL of 5.0% acetic acid was added to the plate, and the plate was left at room temperature for about 10 min to change the color of the Congo red to blue to detect halo formed by the extracellular mannanase activity. In this experiment, the control strain was used as a positive control. About 180 transcription regulatory factor gene disruptants were subjected to screening, and in six strains, a notable reduction in halo was observed (FIG. 3).

In these six strains, one transcription regulatory factor having a Zn$_2$Cys$_6$-type zinc finger motif, which is frequently found in transcription regulatory factors derived from molds and the function of which is unknown, was found (Table 3, TF150). This transcription regulatory factor was defined as a mannan hydrolases transcription regulatory factor and was designated as manR.

TABLE 3

| No. | AO No. | Annotation |
|---|---|---|
| TF012 | AO090026000719 | AN siderophore biosynthesis repressor SREA (GATA zinc finger) |
| TF134 | AO090003000885 | Involved in glucose repression of GAL4p-regulated transcription; Ngglp (HAT?) |
| TF150 | Not predicted | GAL4 YEAST Regulatory protein GAL4 (Zn2Cys6 zinc finger) |
| TF231 | AO090009000459 | AN CpcA, GENERAL Amino acid control transactivator, SC GCN4 (bzip zinc finger) |
| TF204 | AO090120000041 | putative transcriptional regulator [*Schizosaccharomyces pombe*] (Histone-like TF) |
| TF023 | AO090005000270 | zinc-finger protein, BR140-human (PHD finger) |

Example 3

Method of Producing manR Disruptant

The manR disruptant (TF150 disruptant) in the library of the transcription regulatory factor disruptants was produced by the following method. The present inventors anticipated by manual annotation that a transcription regulatory factor gene having one Zn2Cys6-type zinc finger motif lies between 545601 and 543115 in chromosome 8 SC010 of *Aspergillus oryzae* RIB40.

In the production of the library, a vector for gene disruption was designed using the genes that are expected to lie in this region as targets, and oligonucleotide primers represented by SEQ ID NOs: 7 to 12 were designed.

The vector for gene disruption was produced as follows. First, DNA fragments of the right and left arms (fragments R and L) for homologous recombination and of pyrG (fragment P) serving as a marker gene in transformation were amplified by a PCR method.

In the PCR, KOD plus (manufactured by TOYOBO), which has high accuracy, was used. The final concentration of MgSO4 in the reaction solution was adjusted to 1.2 mM in the amplification of fragments R and L and was adjusted to 2.0 mM in the amplification of fragment P, and optionally dimethyl sulfoxide (manufactured by Sigma-Aldrich Japan) was added to the reaction solution at a final concentration of 5.0 to 7.0%.

As the primers for the PCR, a set of primers represented by SEQ ID NOs: 7 and 8 was used in the amplification of fragment L, a set of primers represented by SEQ ID NOs: 11 and 12 was used in the amplification of fragment R, and a set of primers represented by SEQ ID NOs: 9 and 10 was used in the amplification of fragment P.

As the template for the PCR reaction, 150 ng of the genomic DNA of the wild-type strain was used, and the total amount of the reaction system was adjusted to 50 μL.

The PCR reaction was performed at 94° C. for 2 min and then 30 cycles of 94° C. for 10 sec, 55° C. for 15 sec, and 68° C. for 2 min and 30 sec. A part of the amplification product was subjected to electrophoresis on a 0.8% agarose gel to confirm that DNA fragments of about 1.6 kb and about 1.5 kb were amplified in fragments L and R, respectively and that a DNA fragment of about 2.2 kb was amplified in fragment P.

TABLE 4

| No. | Sequence |
|---|---|
| SEQ ID NO: 7 | AGGTGACCTGCAATTTCAATAAACTTTG |
| SEQ ID NO: 8 | <u>GTACGTCTGTTGTCAGCCGAGTCCAGG</u>GATTTTTTCTG |
| SEQ ID NO: 9 | <u>AAATCCCTGGACTCGGCTG</u>ACAACAGACGTACCCTGTGATGTTC |
| SEQ ID NO: 10 | <u>TGGACGGTATATGAGCATACGC</u>AACTGCACCTCAGAAGAAAAGGATG |
| SEQ ID NO: 11 | <u>CTGAGGTGCAGTTGCGTATGCT</u>CATATACCGTCCAACTCTAC |
| SEQ ID NO: 12 | CGTATGGTGAATCACCCTTTGAAACATAC |

The underlined portions in the sequences are sequences added for being used in fusion PCR and are regions that do not anneal to the template DNA in the first-stage PCR.

After the confirmation of the amplification by electrophoresis, all of the remaining DNA fragments of fragments L, R, and P were subjected to electrophoresis on a 0.8% agarose gel and were stained with SYBR green I (manufactured by Takara Bio). Then, the DNA bands were cut out under visible light irradiation in order to prevent the DNA from being damaged.

DNA fragments were purified from the cut-out bands using a Gel Extraction kit (manufactured by QIAGEN), and 1.8 µL of fragment L, 1.8 µL of fragment R, and 5.4 µL of fragment P were mixed. The resulting mixture was used as a template for fusion PCR.

Then, fragments L, R, and P were linked by fusion PCR. In the PCR, KOD plus (manufactured by TOYOBO) was used as in above. The final concentration of $MgSO_4$ in the reaction solution was adjusted to 1.2 mM, and dimethyl sulfoxide (manufactured by Sigma-Aldrich Japan) was added to the reaction solution at a final concentration of 5.0%. As the primers for the PCR, a set of primers represented by SEQ ID NOs: 7 and 12 was used. As the template for the PCR reaction, 9 µL of the solution mixture of fragments L, R, and P prepared above was used, and the reaction system was adjusted to a total amount of 300 µL. The PCR reaction was performed at 94° C. for 2 min and then 30 shuttle cycles consisting of 94° C. for 10 sec and 68° C. for 6 min and 30 sec.

A part of the amplification product was subjected to electrophoresis on a 0.8% agarose gel to confirm that a DNA fragment of about 5 kb was amplified. After the confirmation of the amplification by the PCR reaction, all the remaining reaction solution was subjected to electrophoresis on a 0.8% agarose gel and was stained with SYBR green I (manufactured by Takara Bio). Then, the DNA band was cut out under visible light irradiation in order to prevent the DNA from being damaged. A DNA fragment was purified from the cut-out band using a Gel Extraction kit (manufactured by QIAGEN) and was concentrated by alcohol precipitation. Then, the precipitate was dissolved in 10 µof a TE buffer solution and was used as a vector for manR disruption of a koji mold.

This vector was introduced into the above-described host strain by a common method, i.e., a protoplast-PEG method (Gene, 61: 385, 1987).

The selection of transformants was performed by pyrG positive selection using a Czapek-Dox minimal medium containing 1.2 M sorbitol, but not containing uridine. The disruption of the manR gene in the obtained transformant was confirmed by a PCR method and a Southern hybridization method.

Figure 4:
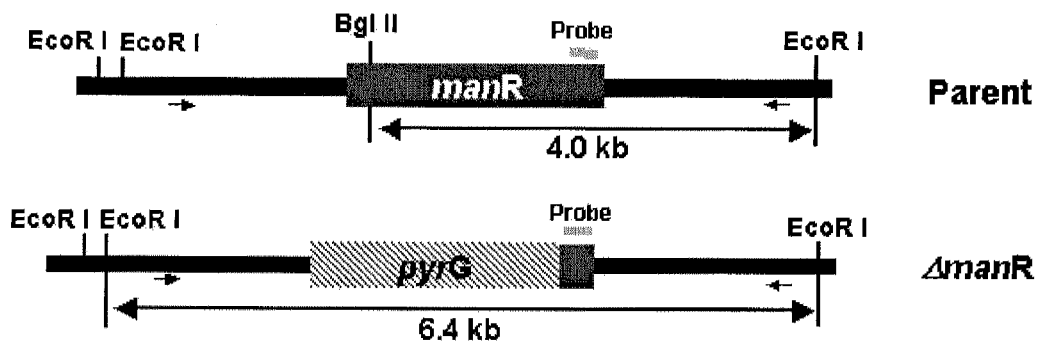
FIG. 4 roughly shows manR gene disruption.

The outline of manR disruption is as shown in FIG. 4.

Preparation of Genomic DNA from manR Disruptant

Whether the target gene region was correctly disrupted in the produced manR disruptant was investigated by a PCR method. The manR disruptant and the host strain were each inoculated to 40 mL of a dextrin-peptone medium in a 150-mL Erlenmeyer flask and were cultured at 30° C. for 3 days at 150 rpm. In the case of culture of the host strain, the medium was supplemented with filtration-sterilized uridine at a final concentration of 15 mM. After completion of the culture, the cells were collected by filtration. Subsequently, genomic DNA was extracted and purified by the same method as in that for genomic DNA described in Example 1.

Example 4

Confirmation of manR Disruptant by PCR Method

PCR was performed using about 150 ng of the genomic DNA of the manR disruptant prepared in accordance with the method described above as the template and using the oligonucleotide primers represented by SEQ ID NOs: 13 and 14. A reaction system using the DNA derived from the host strain as the template was used as a control. ExTaq (manufactured by Takara Bio) was used as the enzyme for PCR, and dimethyl sulfoxide (manufactured by Sigma-Aldrich Japan) was added to the reaction solution at a final concentration of 5.0%. Other conditions were adjusted to those described in the manual attached to the enzyme, and the total amount of the reaction solution was adjusted to 20 µL. The PCR reaction was performed at 94° C. for 2 min and then by 30 shuttle cycles of 94° C. for 10 sec and 68° C. for 8 min.

TABLE 5

| No. | Sequence |
|---|---|
| SEQ ID NO: 13 | ATGAACGGGGCGATGTTCCTTAATAC |
| SEQ ID NO: 14 | GCATACCTGAGCGATGACCCATAGAG |

Figure 5:
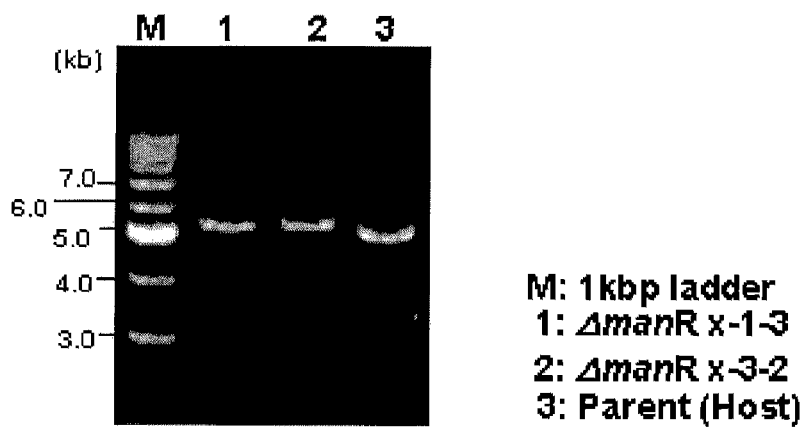
FIG. 5 shows the confirmation results of manR disruption by PCR.

A part of the amplification product was subjected to electrophoresis on a 0.7% agarose gel to confirm that the band of the amplification product derived from the manR disruptant shifted compared with that of the amplification product derived from the host strain. The manR disruptant-derived amplification product was confirmed as a single band. This suggests that the obtained transformant is a homokaryon (FIG. 5).

Example 5

Confirmation of manR Disruptant by Southern Hybridization Method

The transformant was confirmed by Southern hybridization. About 5.0 μg of the genomic DNA of each of the manR disruptant and the host strain was digested by restriction enzymes, EcoRI and BglII, at 37° C. overnight and was then subjected to electrophoresis on a 0.8% agarose gel. The electrophoresed nucleic acids were blotted onto a positively charged nylon membrane, Hybond-N+ (manufactured by GE Healthcare Biosciences), and were subjected to hybridization using a digoxigenin (DIG)-labeled probe at 42° C. overnight. The DIG-labeled probe was produced using a DIG PCR Labeling Kit (manufactured by Roche Diagnostics); ExTaq (manufactured by Takara Bio) was used as the enzyme for PCR; and 100 ng of the genomic DNA of *Aspergillus oryzae* RIB40 was used as the template. The oligonucleotide primers represented by SEQ ID NOs: 15 and 16 were used as the PCR primers, and the total amount of the reaction system was adjusted to 25 μL.

TABLE 6

| No. | Sequence |
| --- | --- |
| SEQ ID NO: 15 | CTACTGTTGCGAGCTGCCAATCTCAAG |
| SEQ ID NO: 16 | CCGTTGTTGGGATATTTCATGGTTTTG |

Figure 6:
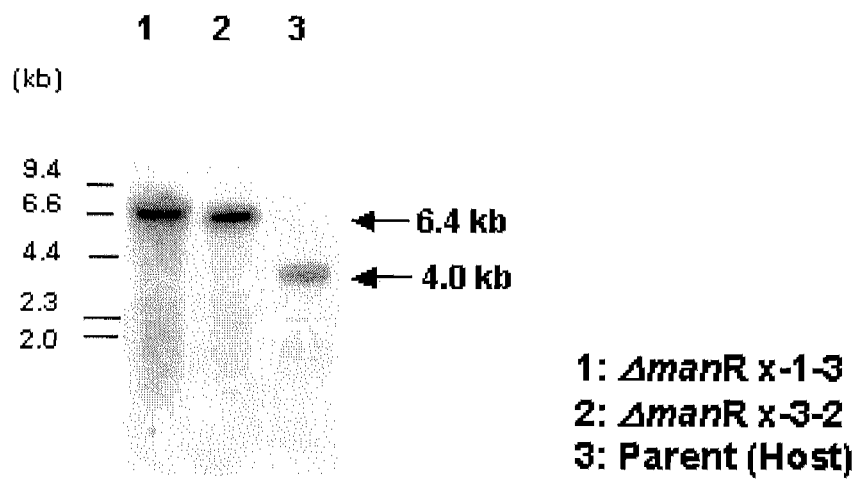
FIG. 6 shows the confirmation results of manR disruption by Southern hybridization.

The reaction was performed at 94° C. for 2 min and then 30 cycles of 94° C. for 10 sec, 55° C. for 15 sec, and 60° C. for 1 min. After completion of the PCR reaction, a part of the reaction solution was subjected to electrophoresis on a 2% agarose gel to confirm that the DIG-labeled nucleotide was incorporated into this PCR product. This DIG-labeled probe was used in hybridization. The washing of the membrane and the detection of signals after the hybridization were performed in accordance with the manual of the DIG system (manufactured by Roche Diagnostics). The results are shown in FIG. 6. In each of the manR disruptant and the host strain, a single band was detected. In the disruptant, the band was observed at about 6.4 kb while the band of the host strain was observed at about 4.0 kb. Thus, an obvious difference between the both was confirmed. The sizes of these bands agreed with the theoretical values. As described above, it was confirmed that the vector for disruption of manR disruptant was correctly introduced and that the nucleus of the disruptant was purified.

Example 6

Influence of manR Disruption on Mannan Degradation Activity During Liquid Culture of Koji Mold In the case that mannanase is produced by a koji mold, *Aspergillus oryzae*, reducing sugars such as monosaccharides and oligosaccharides are produced by degradation of glucomannan, which is a polysaccharide present in the medium. Whether the manR disruption affects the amount of mannanase produced by a koji mold was investigated by measuring the amount of the reducing sugars. Conditions for the experiment were as follows.

About 10,000,000 conidiospores of each of the manR disruptant and the control strain were cultured in 40 mL of a Czapek-Dox minimal medium (3.0% glucose, 0.05% KCl, 0.2% NaNO3, 0.1% KH2PO4, 0.05% MgSO4, 0.001% FeSO4, pH 6.0) in a 150-mL Erlenmeyer flask for 20 hr to germinate. After completion of the culture, the cells were collected by sterilized Mira-Cloth (manufactured by Calbiochem). The collected cells were cultured in a Czapek-Dox minimal medium containing 1.0% glucomannan (manufactured by Megazyme) as a carbon source at 30° C. for 20 hr at 150 rpm, and then the cells were removed by filtration through sterilized Mira-Cloth.

Then, 1.0 mL of the obtained culture solution was transferred to a 1.5-mL plastic microtube and was heated at 100° C. for 10 min to inactivate enzymes present in the medium. The microtube was left at room temperature for 30 min or more for cooling. After the cooling, the amount of the reducing sugars produced in the reaction solution was measured by a Somogyi-Nelson method (J. Biol. Chem., 195, 19, 1952).

Figure 7:
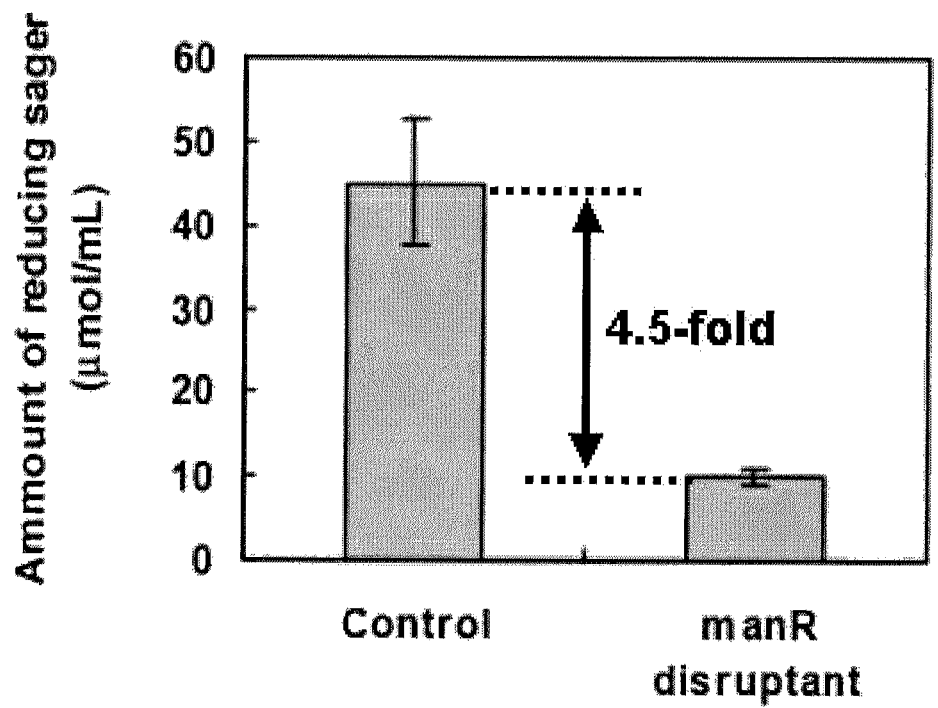
FIG. 7 shows of influence of manR disruption on production of extracellular mannanase by a koji mold.

A standard curve was produced using mannose as a standard. Incidentally, in the quantitative measurement of the reducing sugars, dilution with ultra-pure water was appropriately performed so that the measured value would be within the valid range of the standard curve. The experiment was conducted in independent four runs from the culture in both the disruptant and the control strain. The measurement results are shown in FIG. 7.

The average amount of the produced reducing sugars was 10.0 μmol/ml in the manR disruptant, while the amount in the control strain was 45.1 μmol/ml. Thus, a difference of about 4.5-fold was observed. This difference is probably caused by that the expression amount of mannanase extracellularly secreted is reduced by the disruption of manR to cause a difference in amount of the reducing sugars released from glucomannan. In the manR disruptant, a reduction in activity of extracellular mannanase was confirmed also in a halo assay using a glucomannan plate.

The results described above strongly suggest that manR of a koji mold, *Aspergillus oryzae*, is a factor that positively regulates the expression of extracellular mannan hydrolases.

Example 7

Identification of Mannan Hydrolase Under manR Regulation by DNA Microarray Analysis of manR Disruptant In order to identify a mannan hydrolase gene under regulation by manR, the manR disruptant was subjected to DNA microarray analysis.

First, the total RNA was extracted from a sample. About 10,000,000 conidiospores of each of the manR disruptant and the control strain were cultured in 40 mL of a Czapek-Dox minimal medium in a 150-mL Erlenmeyer flask for 20 hr to germinate.

After completion of the culture, the cells were collected by sterilized Mira-Cloth (manufactured by Calbiochem). The collected cells were cultured in a Czapek-Dox minimal medium containing 1.0% glucomannan (manufactured by Megazyme) as a carbon source at 30° C. for 20 hr at 150 rpm, and then the cells were collected by filtration through sterilized Mira-Cloth, dried by absorbing moisture by a paper towel, and were then rapidly frozen using liquid nitrogen.

Subsequently, the frozen cells were placed in a mortar cooled in advance by pouring liquid nitrogen and were absolutely pulverized with a pestle cooled in advance with liquid nitrogen. Total RNA was extracted from the pulverized cells using an ISOGEN kit (manufactured by Nippon Gene) and was treated with RNase-free DNase I (manufactured by Takara Bio) to degrade mixed DNA and was further purified using an RNeasy Mini column (manufactured by QIAGEN).

After the purification, the concentration and the purity of the RNA were measured using a spectrophotometer GeneSpec III (manufactured by Hitachi), and the quality of the RNA was confirmed by capillary electrophoresis using Bioanalyzer 2100 (manufactured by Agilent Technologies). RNA6000 LabChip was used as the tip of the electrophoresis.

Based on the results of quality check, samples having an RNA Integrity Number (RIN) of 5.8 or more were used for the DNA microarray analysis.

The total RNA obtained by the above-described process was subjected to DNA microarray analysis. The sample was RNA obtained by culturing the manR disruptant, and the control was RNA obtained by culturing the control strain.

The experiment was conducted in independent four runs from the culture in both the disruptant and the control strain. In order to avoid coloring bias, experiment was performed in such a mariner that in two of four arrays, the control strain was placed on the Cy-3 side while the disruptant was placed on the Cy-5 side, and in the remaining two arrays, the colors were swapped. 500 ng of the total RNA was labeled with Cy-3 or Cy-5 using a Low RNA Input Liner Amplification kit (manufactured by Agilent Technologies) in accordance with the manual attached to the kit. Subsequently, the labeled RNA was purified using an RNeasy mini column (manufactured by QIAGEN), and the amount and the quality of the resulting RNA were confirmed, respectively, using a spectrophotometer GeneSpec III (manufactured by Hitachi) and a capillary electrophoresis apparatus Bioanalyzer 2100 (manufactured by Agilent Technologies).

The obtained labeled RNAs each in an amount of 850 ng were mixed and were hybridized to a DNA microarray (Agilent 4×44 K format custom array: manufactured by Noda Institute for Scientific Research) on which all genes of a koji mold were mounted.

The hybridization and washing of the array and the method of scanning were performed in accordance with the manual of Agilent Technologies. The array slide was scanned using a G2505B microarray scanner (manufactured by Agilent Technologies), and the data of the scanning was subjected to digitization and removal of coloring bias using Feature Extraction version 9.5.1 (manufactured by Agilent Technologies).

In the data analysis after the correction, the mean value and the standard deviation of four arrays were mainly used. According to need, commercially available statistical analysis software Agilent GeneSpring version 7.3.1 or a package of free statistical analysis software, R2.4.1. (http://www.r-project.org/) was used.

The outline of the array analysis results is shown in FIG. 8.

In the analysis with this array, the number of genes that significantly expressed in all four arrays was 9,688, which was 74.7% of the whole. On the other hand, the number of genes of which expression was not confirmed or was false positive was 3,285, which was 25.3% of the whole.

Regarding the genes that were confirmed for their significant expression, the manR disruptant was compared with the control strain. The number of genes of which expression was increased more than five-fold was 159 (1.6%), the number of genes of which expression was decreased more than five-fold was 133 (1.4%), and the number of genes of which expression was not changed was 9,396 (97.0%). FIG. 9 shows the top 25 genes in genes of which expression was reduced by manR disruption.

Even the lowest degree of reduction in expression level in the genes listed in FIG. 9 was 13.6-fold (25th place), and the highest degree of the reduction was 44.1-fold (the first place). In the genes listed in FIG. 9, seven genes were of glycoside hydrolases, and two (AO090010000122 and AO090038000444) of the seven genes were anticipated to be genes encoding mannanase classified in glycoside hydrolase family 5 (GH5).

Two genes (AO090005000740 and AO090010000208) were genes encoding mannosidase classified in glycoside hydrolase family 2 (GH2), which degrades manno-oligosaccharides.

One gene (AO090003001305) was a gene encoding α-galactosidase classified in glycoside hydrolase family 27 (GH27), which hydrolyzes galactose binding to a side chain of galactomannan. The results above suggest that manR is a transcription regulatory factor comprehensively regulating enzymes involving in hydrolysis of mannans.

Example 8

Functional Analysis of Mannan Hydrolases that are Anticipated to be Regulated by manR Five mannan hydrolases genes that were suggested to be under regulation of manR by the DNA microarray analysis were expressed in a yeast, *Saccharomyces cerevisiae*, as polyhistidine-tagged proteins. The proteins were investigated for whether they actually function as mannan hydrolases. Oligonucleotide primers that were used are shown in Table 7.

TABLE 7

| No. | Sequence |
|---|---|
| SEQ ID NO: 17 | AAGATCTAAAAAAAAAATGAAATTCCGTAACCTTTTCTTTGCTG |
| SEQ ID NO: 18 | CCTCGAGCCCCAGGTATGCCTGCAGAACGTCCA |
| SEQ ID NO: 19 | GGGATCCAAAAAAAAAATGAAGCTTAACCCTTCACTCCTCAC |
| SEQ ID NO: 20 | CCTCGAGCTTACGACTGTTGATGGCCGCAATATG |
| SEQ ID NO: 21 | CGGATCCAAAAAAAAAATGGCGGCATTCTCTCAGTACCCTCTATC |
| SEQ ID NO: 22 | CCTCGAGCTGGCCAAGATACTTGTACTTCAGAGGAGC |
| SEQ ID NO: 23 | CGGATCCAAAAAAAAAATGTCCGGCTTCAAGTCGCTCGAGCTCTC |

TABLE 7-continued

| No. | Sequence |
|---|---|
| SEQ ID NO: 24 | <u>*CGTCGA*C</u>TAGTCTGTCATCCCCAATGTATGTCCAAC |
| SEQ ID NO: 25 | <u>*CGGATCC*AAAAAAAAA</u>ATGCAGCGTTACATTTCTTTATCCGTGTC |
| SEQ ID NO: 26 | <u>*CCTCGAG*G</u>CATGATTCTCCCACCACCAGAGCAGCAA |

The added sequences not involving in annealing are indicated by underlines, and the restriction enzyme sites for being incorporated in a vector for yeast expression are indicated by italic letters. In the forward primer, nine "A" bases were introduced before the initiator codon in order to improve the translation efficiency.

Then, the gene to be expressed was amplified by RT-PCR using the above-mentioned oligonucleotide primers. First, the control strain was cultured in a 1.0% glucomannan medium by a method shown in Example 6. Total RNA was collected from the cells, and the concentration and the quality were confirmed.

A reverse transcription reaction was performed using 100 ng of this total RNA as the template with PrimeScript Reverse Transcriptase (manufactured by Takara Bio). The composition of the reaction solution was prepared in accordance with the manual attached to the enzyme, and oligo dT primer of the kit was used as the oligonucleotide primer for the reverse transcription. The reaction was conducted at the total amount of 20 µL. The reverse transcription reaction was performed at 50° C. for 30 min, and the reverse transcriptase was inactivated by heating at 70° C. for 10 min. Then, the sample was stored at 4° C. till the use. As the enzyme for PCR, KOD plus DNA polymerase (manufactured by TOYOBO), which has high accuracy, was used. Dimethyl sulfoxide (manufactured by Sigma-Aldrich Japan) for molecular biology was added to the reaction system at a final concentration of 5.0%. Other reaction conditions were adjusted to those shown in the manual attached to the enzyme, and 1.0 µL of the above-described cDNA was added as a template DNA, and the oligonucleotide primers were each added in a final concentration of 1.0 µM. The reaction was performed at a total amount of 50 µL.

The combinations of the oligonucleotide primers were SEQ ID NOs: 17 and 18 in the amplification of AO090038000444, SEQ ID NOs: 19 and 20 in the amplification of AO090010000122, SEQ ID NOs: 21 and 22 in the amplification of AO090010000208, SEQ ID NOs: 23 and 24 in the amplification of AO090005000740, and SEQ ID NOs: 25 and 26 in the amplification of AO090003001305. The PCR reaction was performed at 94° C. for 2 min and then 30 cycles of 94° C. for 10 sec, 58° C. for 15 sec, and 72° C. for 4 min 00 sec.

After completion of the reaction, a part of the reaction solution was subjected to electrophoresis on a 0.8% agarose gel to confirm that products according to the purposes were amplified. After the confirmation, all the remaining reaction solution was subjected to electrophoresis on a 0.8% agarose gel and was stained with SYBR green I (manufactured by Takara Bio). Then, the DNA band with a target size was cut out under visible light irradiation in order to prevent the DNA from being damaged.

A DNA fragment was purified from the cut-out band using a Gene CleanII kit (manufactured by QBiogene). Then, the purified DNA fragment was blunted and phosphorylated using a TaKaRa Mighty Cloning kit (Blunt end, manufactured by Takara Bio), and then was ligated to the Hindi site of pUC118.

After the ligation reaction, the plasmid obtained by the reaction was introduced to *E. coli* JM109 strain to obtain a transformant. Plasmid was extracted and purified from this transformant using a QIAprep Spin Mini Prep kit (manufactured by QIAGEN).

Then, 50 ng of the obtained plasmid was digested by restriction enzyme BamHI and was subjected to electrophoresis on a 0.8% agarose gel to select the plasmid to which the target DNA fragment was linked. In the plasmid in which an insert was inserted, oligonucleotide primers that were used in amplification of a target sequence were used, and analysis of the base sequence was performed by a Sanger method to confirm that no mutation was introduced in the obtained gene.

The obtained plasmids were designated as follows. The plasmid obtained by subcloning AO090038000444 was designated as pUC-AomanA, the plasmid obtained by subcloning AO090010000122 was designated as pUC-AomanB, the plasmid obtained by subcloning AO090010000208 designated as pUC-AomndA, the plasmid obtained by subcloning AO090005000740 was designated as pUC-AomndB, and the plasmid obtained by subcloning AO090003001305 was designated as pUC-AoagaA.

Next, vectors for expressing target proteins in a yeast, *Saccharomyces cerevisiae*, were constructed. First, 1.5 µg of each of five types of plasmids in which target genes were inserted in pUC118 described in Example 8 was digested by a restriction enzyme to cut out the insert inserted in each plasmid. In the case of digesting pUC-AomanA, pUC-AomndB, and pUC-AoagaA, BamHI and XhoI were used as the restriction enzymes. In the case of digesting pUC-AomanB, BglII and XhoI were used as the restriction enzymes. In the case of digesting pUC-AomndB, BamHI and SalI were used as the restriction enzymes. The digestion was performed at 37° C. overnight. After the completion of the reaction, the reaction solution was subjected to electrophoresis on a 0.8% agarose gel, and the insert DNA fragment was purified by the method described above.

Figure 10:
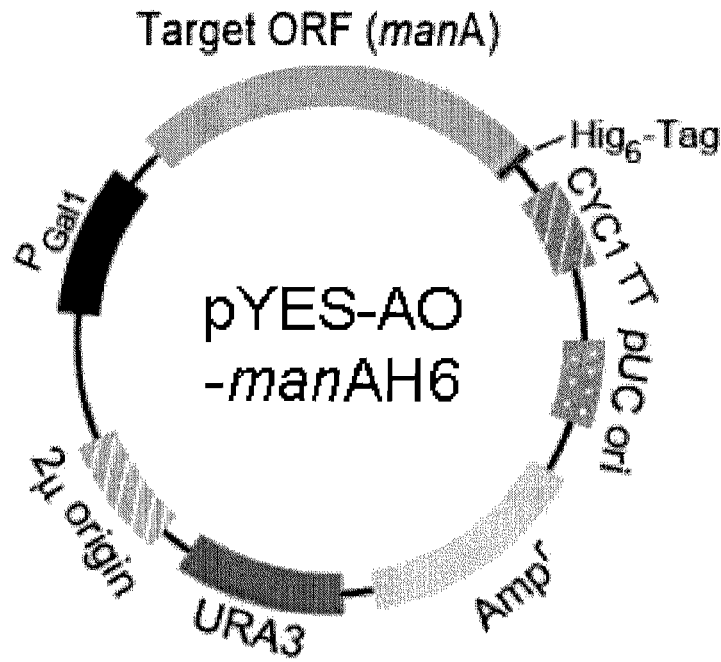
FIG. 10 shows the structure of pYES-AO-manAH6, a vector for yeast expression.

The each purified fragment was digested and dephosphorylated by BamHI and XhoI, and then ligated to a purified yeast/*E. coli* shuttle vector pYES2/CT (manufactured by Invitrogen) to select and confirm the plasmid in accordance with the method of confirming plasmid described in the insertion of target gene into pUC118 in Example 8. The pYES2/CT includes a region encoding URA3, a GAL1 promoter, a CYC1 terminator, and a polyhistidine tag for a selection marker. This polyhistidine tag region was incorporated so as to form a fusion protein with the target gene. The produced plasmids were designated as follows. The vector for AO090038000444 expression was designated as pYES-AO-manAH6, the vector for AO090010000122 expression was designated as pYES-AO-manBH6, the vector for AO090010000208 expression was designated as pYES-AO-mndAH6, the vector for AO090005000740 expression was designated as pYES-AO-mndBH6, and the vector for AO090003001305 expression was designated as pYES-AO-agaAH6. As an example of the vector for yeast expression, the structure of pYES-AO-manAH6 is shown in FIG. 10. The structures of other four types of vectors are basically the same as that of pYES-AO-manAH6, and only the portion of ORF to be expressed is different.

Example 9

Introduction of Expression Vector to *Saccharomyces cerevisiae* INVSc1 Strain

The *Saccharomyces cerevisiae* INVSc1 strain is a strain having an uracil auxotrophic ura3-52 mutation and can be transformed with a pYES2/CT vector having ura3. Competent cells of this microorganism strain were produced using an S.c.Easy yeast competent cell production kit (manufactured by Invitrogen). The five types of expression vectors for mannan hydrolases described in Example 8 were introduced into the competent cells, and selection on an SC minimal medium not containing uracil was conducted to obtain respective transformants. The produced microorganism strains were designated as follows. The AO090038000444 expression strain was designated as an INV-AO-manA strain, the AO090010000122 expression strain was designated as an INV-AO-manB strain, the AO090010000208 expression strain was designated as an INV-AO-mndA strain, the AO090005000740 expression strain was designated as an INV-AO-mndB strain, and the AO090003001305 expression strain was designated as an INV-AO-agaA strain.

In addition, as a control for a yeast expression experiment, an INVSc1/pYES2lacZ strain that is an INVSc1 strain including pYES2/CT/lacZ (a plasmid having a lacZ gene incorporated in a vector) was produced.

Example 10

Expression, Purification, and Measurement of Activity of Polyhistidine-Fused Protein The five types of fusion protein expressing strains produced in Example 9 and the INVSc1/pYES2lacZ strain as a control were cultured to obtain polyhistidine-tagged proteins. The procedure is as follows.

First, each strain was applied to an SC minimal agar medium containing 2% glucose but not containing uracil using a platinum loop and was cultured at 30° C. for 4 days to obtain colonies. These colonies were inoculated to 20 mL of an SC minimal medium containing 2% of raffinose but not containing uracil and were subjected to shaking culture at 30° C. for 48 hr at 180 rpm. After completion of the culture, the absorbance of each culture solution was measured at 600 nm. The culture solution was put in a sterile centrifuge tube in an amount that gives an absorbance of 0.4 when the culture solution was inoculated in 50 mL of an induction medium, and the supernatant was removed by centrifugation. The obtained cells were suspended in 50 mL of an SC medium (induction medium) containing 2% galactose but not containing uracil and were subjected to shaking culture at 30° C. for 24 hr at 180 rpm. After completion of the culture, the entire culture solution was centrifuged to collect the cells as precipitate. The precipitate was washed with 10 mL of cool water, and the collected cells were stored at −80° C.

Example 11

Yeast cells were pulverized with a FastPROTEIN RED kit (manufactured by MPBio Japan). First, one tablet of Complete Mini EDTA-free (protease inhibitor cocktail, manufactured by Roche Diagnostics) was dissolved in 10 mL of a yeast breaking buffer, and resulting solution was stored on ice till the use (hereinafter, this solution is referred to as YBB+PI). Then, the cryopreserved cells were gently thawed on ice, and 2.0 mL of the cells (about 300 to 400 mg) were suspended in YBB+PI. About 1.2 mL of the resulting suspension was dispensed in each of two 2-mL tubes having a screw cap and containing acid-washed glass beads. The suspension in each tube was vigorously stirred with a vortex mixer at 4° C. for 1 min and then cooled on ice for 1 min. This procedure was repeated five times to pulverize the cells. After the pulverization, the glass beads and the remains of the cells were removed by centrifugation at 10,000×g for 10 min at 4° C. To the supernatant, an equivalent amount of a 3 M NaCl/100 mM sodium phosphate buffer solution (pH 7.4) containing 40 mM imidazole was added. The resulting mixture was gently mixed and was then applied to a 1-mL HisTrapHP column (nickel affinity column, manufactured by GE Healthcare Biosciences) equilibrated in advance with a 1.5 M NaCl/50 mM sodium phosphate buffer solution (pH 7.4) containing 20 mM imidazole. This column was washed with 20 mL of the same buffer solution as that used for equilibration and the target protein was then eluted with 5 mL of a 1.5 M NaCl/50 mM sodium phosphate buffer solution (pH 7.4) containing 500 mM imidazole. Furthermore, the eluted fraction was concentrated and desalted using Microcon YM30 (ultrafiltration equipment, molecular weight cut-off: 30,000, manufactured by Millipore).

Example 12

The Glycoside Hydrolase Activity of Each Purified and Concentrated Polyhistidine-Fused Protein was Measured as Follows First, the mannanase activity of each sample was measured by the following method. 50 μL of the concentrated and desalted sample was added to 50 μL, of a substrate solution prepared by dissolving 2% (W/V) Azo-Carob-Galactomannan (manufactured by Megazyme) in a 50 mM sodium acetate buffer solution (pH 5.0). The resulting mixture was stirred with a vortex mixer for 5 sec and was allowed to react at 37° C. for 1 hr. The reaction was stopped by adding 250 μL of 99.5% ethanol to the reaction solution, and then the solution was left to stand at room temperature for 10 min. Furthermore, this solution was centrifuged at 500×g for 10 min to precipitate unreacted macromolecular substances. The absorbance of the supernatant was measured at 590 nm, which is the absorption maximum of azo dye released by hydrolysis, to quantitatively measure the mannanase activity. Separately, an enzyme solution was treated at 100° C. for 10 min to inactivate the enzyme in advance, and this solution was applied to the same reaction as that of the sample, and the measured value was used as the blank value of each sample.

The mannosidase activity of each sample was measured by the following method. To 30 μL of a concentrated and desalted sample, 30 μL of a 50 mM sodium phosphate buffer solution (pH 7.0) and 40 μL of 2.5 mM p-nitrophenyl-β-D-mannopyranoside (manufactured by Sigma-Aldrich) were added. The resulting mixture was subjected to a reaction at 37° C. for 12 hr. The reaction was stopped by adding 100 μL of a 500 mM sodium carbonate solution to the reaction solution. The absorbance was measured at 405 nm, which is the absorption maximum of p-nitrophenol released by hydrolysis, to quantitatively measure the mannosidase activity. As a blank, a 50 mM sodium phosphate buffer solution (pH 7.0) was used instead of the sample, and the amount of autolysis of the substrate was measured.

The α-galactosidase activity of each sample was measured by the following method. First, each sample was diluted 20-fold with a 50 mM sodium acetate buffer solution (pH 5.0). To 20 µL of each diluted sample, 40 µL of a 50 mM sodium acetate buffer solution (pH 5.0) and 40 µL of 2.5 mM p-nitrophenyl-α-D-galactopyranoside (manufactured by Wako Pure Chemical Industries) were added. The resulting mixture was subjected to a reaction at 37° C. for 30 min. The reaction was stopped by adding 100 µL of a 500 mM sodium carbonate solution to the reaction solution. The absorbance was measured at 405 nm, which is the absorption maximum of p-nitrophenol released by hydrolysis, to quantitatively measure the α-galactosidase activity. As a blank, a 50 mM sodium acetate buffer solution (pH 5.0) was used instead of the sample, and the amount of autolysis of the substrate was measured. After the measurement, the enzyme activity of the undiluted sample was calculated by multiplying the value (ΔOD405 nm) obtained by subtracting the blank value from the measured value by 20, which is the dilution rate.

Figure 11:
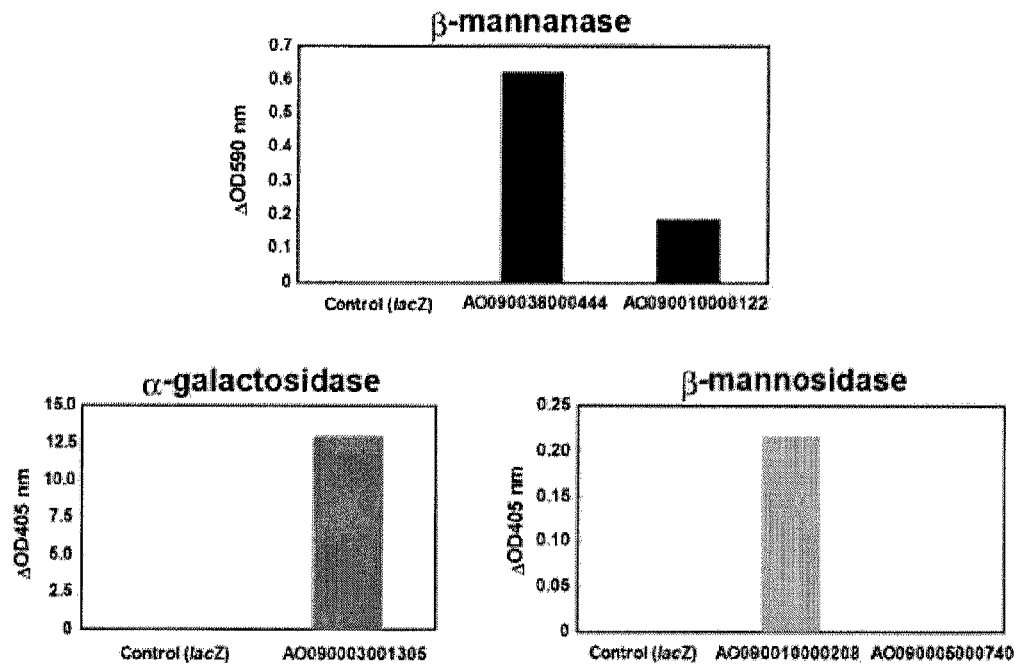
FIG. 11 shows the activities of koji-mold mannan hydrolases expressed by yeast.

The results of the activity measurement are shown in FIG. 11. The INVSc1/pYES2lacZ strain used as the expression control showed high β-galactosidase activity, but did not show mannanase, mannosidase, and α-galactosidase activities. This revealed that mannanase, mannosidase, and α-galactosidase derived from yeasts are not contained in the fraction purified using a His-Trap-HP column. Furthermore, both AO090038000444 and AO090010000122 showed significant activities when they were investigated for mannanase activities; AO090010000208 showed a significant mannosidase activity, whereas AO090005000740 did not show the activity when they were investigated for mannosidase activity, and both AO090010000208 and AO090005000740 did not show mannanase activities; and AO090003001305 had very high activity when it was investigated for α-galactosidase activity.

Combination of the actions of these four genes that have been confirmed to have activities by this example makes it possible to degrade galactomannan having side chains to monosaccharides, i.e., mannose and galactose. This revealed that manR is a transcription regulatory factor that allows koji molds to comprehensively regulate expression of glycoside hydrolases necessary for degradation of galactomannan, which is widely present in the natural world.

Example 13

Sequence Analysis of Spliced Transcription Product of manR

In order to investigate the sequence of a transcription product of the manR gene after splicing (removal of intron), RT-PCR was performed, and the base sequence of the resulting cDNA fragment was analyzed. First, the control strain was cultured in a Czapek-Dox medium containing 1.0% glucomannan as a carbon source by the same method as that described in Example 6, and the concentration and the quality of total RNA collected from the cells were confirmed.

A reverse transcription reaction was performed using 100 ng of this total RNA as the template with PrimeScript Reverse Transcriptase (manufactured by Takara Bio) to obtain cDNA derived from mRNA after splicing (removal of intron). The composition of the reaction solution was prepared in accordance with the manual attached to the enzyme, and oligo dT primer of the kit was used as the oligonucleotide primer for the reverse transcription. The reaction was performed at a total amount of 20 µL. The reverse transcription reaction was performed at 50° C. for 30 min, and the reverse transcriptase was inactivated by heating at 70° C. for 10 min. Then, the sample was stored at 4° C. till the subsequent PCR.

PCR was performed using the above-described cDNA as a template. KOD plus (manufactured by TOYOBO), which has high accuracy, was used as an enzyme for the PCR, and dimethyl sulfoxide (manufactured by Sigma-Aldrich Japan) was added to the reaction system at a final concentration of 5.0%.

Other reaction conditions were adjusted to those shown in the manual attached to the enzyme, and 1.0 µL of the cDNA serving as a template was added, and the reaction was performed at a total amount of 50 µL.

Figure 12:
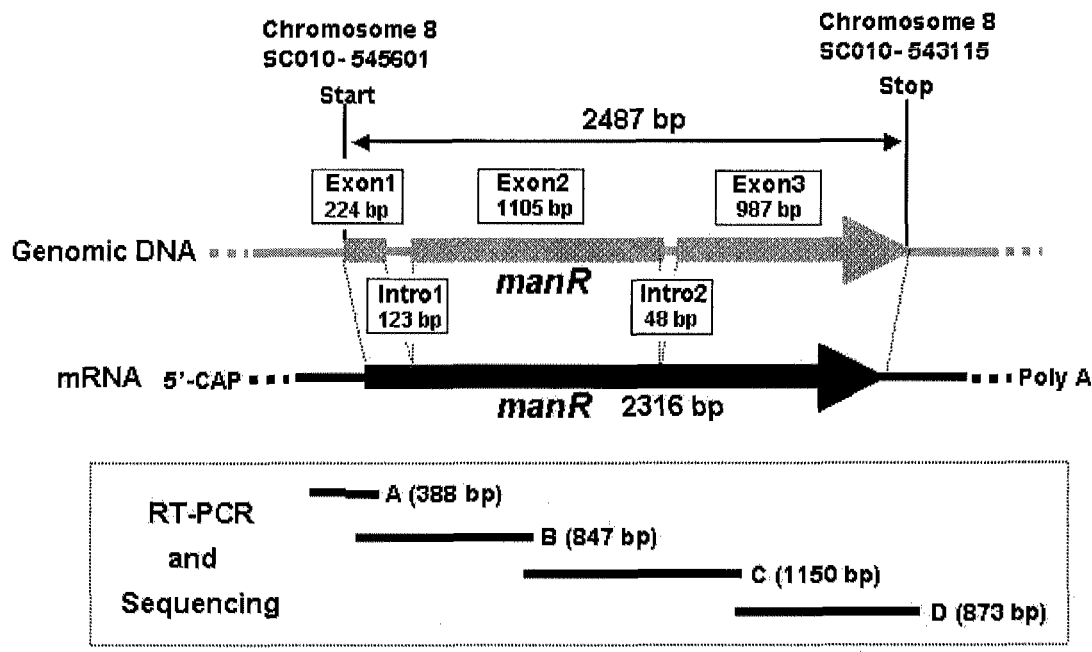
FIG. 12 roughly shows the structures of the manR gene and its transcription product.

The PCR reaction was performed at 94° C. for 2 min and then 30 cycles of 94° C. for 10 sec, 55° C. for 15 sec, and 68° C. for 2 min. Their outlines of the four fragments (fragments A, B, C, and D) amplified by RT-PCR are shown in FIG. 12.

As the oligonucleotide primers, the primers represented by SEQ ID NOs: 27 and 28 were used in the amplification of fragment A, the primers represented by SEQ ID NOs: 29 and 30 were used in the amplification of fragment B, the primers SEQ ID NOs: 31 and 32 were used in the amplification of fragment C, and the primers represented by SEQ ID NOs: 33 and 34 were used in the amplification of fragment D.

TABLE 8

| No. | Sequence |
|---|---|
| SEQ ID NO: 27 | AATCTGCAGGGTCTCACTTCTAGTACGCTG |
| SEQ ID NO: 28 | CCGTCACACTTGATCTTGCGATGTCTG |
| SEQ ID NO: 29 | AGCTGAGTGGGTGTCTTCTGTTTATCATTG |
| SEQ ID NO: 30 | GCATCTCTGTTACTGGTCGATGTGGTTG |
| SEQ ID NO: 31 | ACAGACTCCAGGGACTCAGCTCTAGGATAC |
| SEQ ID NO: 32 | AACTTGAGATTGGCAGCTCGCAACAGT |
| SEQ ID NO: 33 | GAGGCTACAATTCAAGACATTTCTTCAAC |
| SEQ ID NO: 34 | AAACTGATGATCATTCATACACTATATG |

A part of each reaction solution was subjected to electrophoresis using a 1.5% agarose gel to confirm that a product of about 400 bp was amplified in fragment A, a product of about 850 bp was amplified in fragment B, a product of about 1200 bp was amplified in fragment C, and a product of about 900 bp was amplified in fragment D.

After the confirmation of the amplification, all the remaining PCR products in fragments A, B, C, and D were each subjected to electrophoresis on a 1.5% agarose gel to purify the DNA fragment by the gel extraction. Then, the obtained fragment was subjected to DNA sequence analysis by a Sanger method. In the base sequence analysis of each DNA fragment, the base sequence was determined from both sides of a target sequence using the amplified fragments as the primers. The procedure of determining the base sequence was entrusted to Bio Matrix Research, Inc.

The results of DNA sequence analysis of the obtained four RT-PCR products showed that the sequences of fragments A and D completely agree with the sequence of genomic DNA of *Aspergillus oryzae* RIB40, which has been already published, while the sequences of fragments B and C have deletion portions of 123 bp and 48 bp, compared with the genomic DNA of *Aspergillus oryzae* RIB40, which has been already published, but other base sequences completely agree with the sequence of the genomic DNA. Both the genomic DNA sequences corresponding to the deletion portions of the two fragments have sequences that start with GT and end with AG, characteristic to introns, (GT-AG rule). These results reveal that the manR gene in the genome includes two introns of 123 bp and 48 bp. The results also show that the sequence of the manR transcription product represented by SEQ ID NO: 1 is that derived from mRNA actually expressed in the microorganism strain and is not derived from a contaminated genome.

Furthermore, these four fragment sequences were unified to one sequence based on portions that overlap between the fragments, and analysis was further promoted. The results show that the obtained unified sequence after splicing (removal of intron) includes an open reading frame (ORF) of 2,316 bp. This ORF was compared with the base sequence of the genome of *Aspergillus oryzae* RIB40, which has been published, and was thereby confirmed that the position of the initiator codon of the ORF corresponds to 545601 in the chromosome 8 SC010, which is the same as the results of manual annotation of manR and also the position of the terminator codon agrees with the anticipated region of manR (SC010-543115). The base sequence of cDNA derived from a manR transcription product after splicing (removal of intron) obtained by this analysis is shown in SEQ ID NO: 1.

The base sequence of SEQ ID NO: 1 was analyzed using GENETYX version 9 (manufactured by Genetics), and, as a result, it was expected that this DNA encodes a protein composed of 771 amino acids and having an estimated molecular weight of 86.5 kDa. This amino acid sequence is shown in SEQ ID NO: 2.

Cloning of Full Length of manR Transcription Product after Splicing

RT-PCR was performed for obtaining the full-length of the spliced manR transcription product represented by SEQ ID NO: 1. Based on the base sequence information obtained by the analysis described above, the oligonucleotide primers represented by SEQ ID NOs: 35 and 36 were designed.

TABLE 9

| No. | Sequence |
|---|---|
| SEQ ID NO: 35 | AGCTGAGTGGGTGTCTTCTGTTTATCATTG |
| SEQ ID NO: 36 | TAGTGCCCTTAACCAGAAGGGCTAGATG |

As the enzyme for PCR, PrimeScript DNA polymerase (manufactured by Takara Bio), which has high accuracy, was used. The composition of the reaction system was adjusted according to the manual attached to the enzyme, and 1.0 µL of the cDNA prepared in the reverse transcription reaction in Example 13 was added as a template DNA, and the oligonucleotide primers represented by SEQ ID NOs: 35 and 36 were each added in a final concentration of 1.0 µM. The reaction was performed at a total amount of 50 µL.

The PCR reaction was performed at 94° C. for 1 min and then 38 cycles of 94° C. for 10 sec, 55° C. for 15 sec, and 72° C. for 4 min. After the completion of the reaction, a part of the reaction solution was subjected to electrophoresis on a 0.8% agarose gel to confirm that aDNA fragment of about 2.5 kb was amplified.

After completion of the confirmation, all the remaining reaction solution was subjected to electrophoresis on a 0.8% agarose gel, and the DNA fragment was purified by gel extraction. The purified DNA fragment was blunted and phosphorylated using a TaKaRa Mighty Cloning kit (Blunt end, manufactured by Takara Bio), and then was ligated to the HincII site of pUC118.

After the ligation reaction, the plasmid obtained by the reaction was introduced to *E. coli* JM109 strain to obtain a transformant. Plasmid was extracted and purified from this transformant using a QIAprep Spin Mini Prep kit (manufactured by QIAGEN). Then, 50 ng of the resulting plasmid was digested by restriction enzyme EcoRI (manufactured by Nippon Gene) and then subjected to electrophoresis on a 0.8% agarose gel. Plasmids showing a band at about 6.0 kb were selected as those having an insert.

One of the selected plasmids was subjected to base sequence analysis by a Sanger method using the oligonucleotide primers represented by SEQ ID NOs: 27 to 36. It was confirmed from the results that the DNA fragment inserted into the obtained plasmid was cDNA derived from the full-length of the manR transcription product after splicing (removal of intron) and that no mutation was caused by the PCR. The pUC118 in which this spliced full-length manR gene was inserted was designated as pAOmanR-c2.5. In this Example, total RNA was obtained from the control strain. The control strain is a derivative of a wild-type strain, and the sequence of the manR region is completely the same as that of the wild-type strain. Accordingly, it is possible to obtain the spliced manR transcription product having completely the same base sequence as that of SEQ ID NO: 1 by using the wild-type strain instead of the control strain.

Example 14

The amino acid sequence of the manR gene product (ManR) represented by SEQ ID NO: 2 was analyzed by a motif search method using a hidden Markov model developed by Finn, et al., Pfam 23.0 (Nucleic Acids Res., Database Issue 36, D281, 2008) to search a significant motif present in ManR.

As a result, it was revealed that ManR includes two significant motifs. One significant motif was a Zn_Clus, Fungal Zn(2)-Cys(6) binuclear cluster domain of Pfam00172 and was present from the 35th residue to the 72nd residue of ManR (35-TLRACTSCRHRKIKCDGEKPCEACRW-YKKADQCHYADPRP-72 (SEQ ID No: 50), six cysteine residues that are typically present in Zn2Cys6 zinc finger motif are indicated by underlines). The E-value was 4e-05. The other significant motif was a Fungal_trans,Fungal specific transcription factor domain of Pfam04082 and was present from the 341st residue to the 439th residue of ManR (341-HIETIQTLGLLGGQYLHYVSQPNLAY-SLMGAALRMAAALGLHKEFSDNQEGSCKQNIYS TDLKRRVWWSLFCLDTWGC-MTLGRPSMGRFGPTITVKLPQ-439)(SEQ ID NO: 51). The E-value was 2e-06. The results of this analysis suggest that ManR is a transcription regulatory factor that is specific to molds and has a DNA binding site of $Zn_2Cys_6$ zinc finger motif.

Example 15

Estimation of Intracellular Localization of manR Gene Product by PSORTII

The intracellular localization of the protein was estimated using the deduced amino acid sequence of the manR gene product (ManR) represented by SEQ ID NO: 2 by PSORTII (http://psort.ims.u-tokyo.ac.jp/) developed by Nakai, et al.

As a result, the probability of existing in the nucleus was 34.8%, the probability of existing in the cytoplasmic membrane was 21.7%, and the probability of existing in the vacuole was 17.4%. On the other hand, the probabilities of that ManR was localized in the endoplasmic reticulum, the mitochondria, the Golgi body, and the extracellular secretory vesicle were each 10.0% or less.

As described above, in the estimation results, the pobability of that ManR was localized in the nucleus was highest. The results of the pfam search described above estimated that ManR is a transcription regulatory factor that has a Zn2Cys6 zinc finger motif specific to molds. Accordingly, the estimation result that the probability of that ManR is localized in the nucleus is high is believed to be a rational result.

Example 16

Identity Search of manR Gene Product (Protein)

A known amino acid sequence database was searched for a sequence having a high sequence identity to the amino acid sequence of ManR represented by SEQ ID NO: 2. The search was performed using NCBI blastp (http://www.ncbi.nlm.nih.gov/BLAST/), and nr was used as the database.

As a result, no sequence that agreed with the query sequence was found, and putative C6 transcription factor (GenBank: EAW10989) of *Aspergillus clavatus* NRRL 1 showed the highest identity of 71%.

Putative C6 transcription factor putative (GenBank: EAW20871) of Neosartorya fischeri NRRL181 and conserved hypothetical protein (GenBank: EAU30817) of *Aspergillus terreus* NIH2624 each showed a high identity of 71%, which was almost the same as that of putative C6 transcription factor derived from *Aspergillus clavatus*.

Some of these proteins exhibiting high identity were anticipated to be transcription regulatory factors, but there was no protein of which target has been revealed. In addition, no protein showing a high identity of 70% or more was found, other than the three proteins. Furthermore, proteins having an E-value of 1.0e-15 or less were searched for their functions, but there was no protein the function thereof has been revealed.

Identity Search of manR Gene (Nucleic Acid)

A sequence having a high sequence identity to the base sequence represented by SEQ ID NO: 1 was serarched. The search was performed using NCBI blastn (http://www.ncbi.nlm.nih.gov/BLAST/), and nr was used as the database.

As a result, the sequence present in the chromosome 8 SC010 of *Aspergillus oryzae* RIB40, which was the source of the manR gene, completely agreed with the query sequence and covered 100% of the query sequence.

Putative C6 transcription factor (GenBank: EAW20871) of Neosartorya fischeri NRRL181 showed next high identity and covered 87% of the query sequence. The portion of the highest identity showed a homology of 76%. Putative C6 transcription factor (GenBank: EAW10989) of *Aspergillus clavatus* NRRL 1 showed next high identity and covered 87% of the query sequence. The portion of the highest identity showed a homology of 75%.

Conserved hypothetical protein (GenBank: EAU30817) of *Aspergillus terreus* NIH2624, which showed high identity in the identity search of protein together with the above-mentioned two strain, also covered 81% of the query sequence, and the portion of the highest identity showed a homology of 69%. Thus, the base sequence also exhibited some high identity, but the value was slightly low compared with the results of the protein comparison.

In the case of identity search of base sequence, genes having an E-value of 1.0e-15 or less were searched for their functions, but there was no gene the function of which has been revealed.

It was confirmed from the results above that the manR gene represented by SEQ ID NO: 1 and the ManR protein represented by SEQ ID NO: 2 of the present invention have been first to be revealed their functions among these similar genes.

Example 17

Type and Positional Relation of Genes Adjacent to manR

Figure 13:
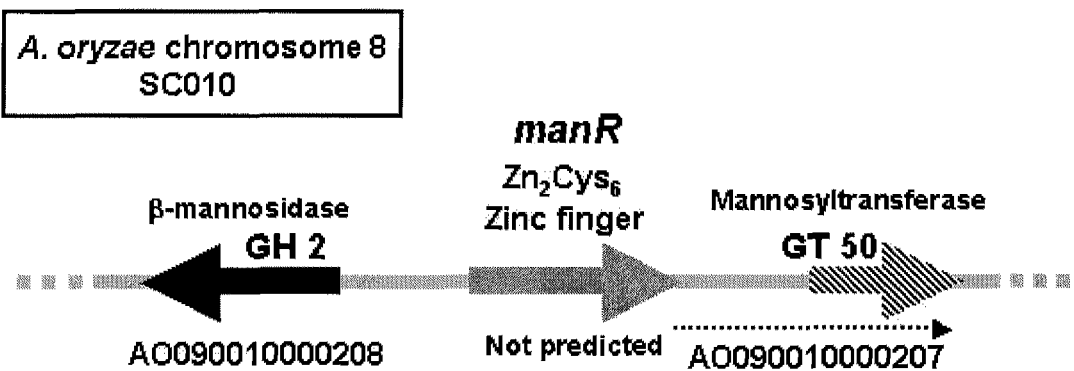
FIG. 13 shows the position of manR on koji mold genomic DNA.

FIG. 13 roughly shows the results of investigation of the manR gene on the genome and genes located upstream and downstream near the manR gene. The manR gene was located between AO090010000208, which is the mannosidase gene, and AO090010000207, which is anticipated to be mannosyltransferase.

It was shown that the region near the 3'-terminal of manR overlaps AO090010000207. However, the gene region of AO090010000207 was compared with anticipated gene information on related species by a program such as BlastX or tBlastN, and anticipation was performed again by manual annotation. As a result, it was anticipated that the probability of that the position of the initiator codon was present on the downstream side of AO090010000207 was high and that the possibility of that manR and the ORF of the gene adjacent to manR on the downstream side overlaps is low.

Based on the anticipation results described above, there is a possibility that manR is present between the mannosidase gene and the mannosyltransferase gene and forms a cluster as a mannose metabolic system, and it is suggested that manR is a gene participating in the mannan metabolic system.

Example 18

Forced Expression of manR Gene in Koji Mold

Figure 14:
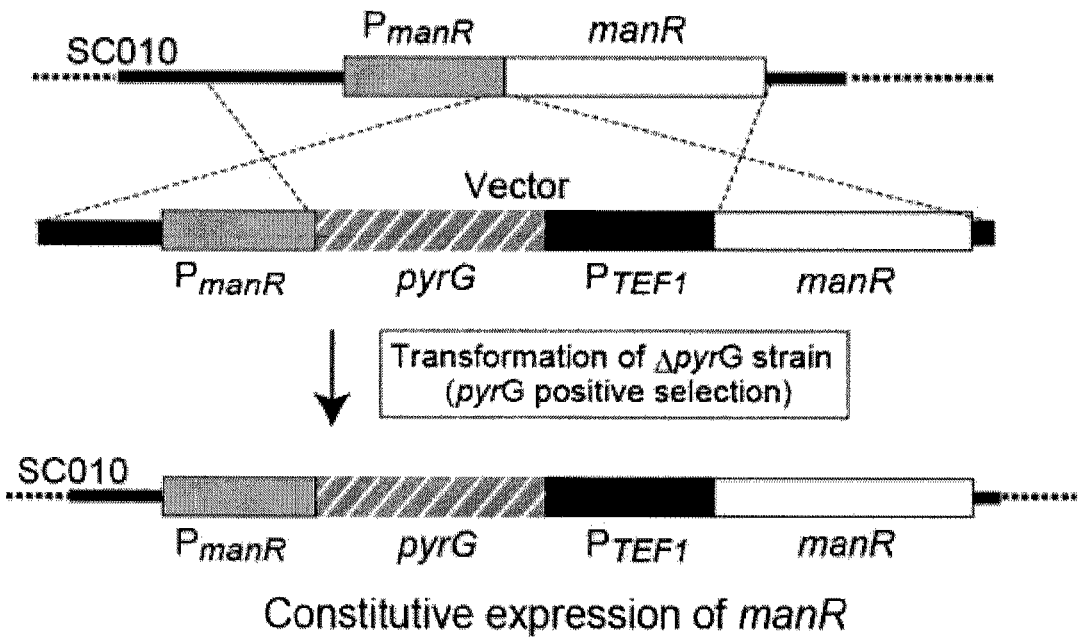
FIG. 14 shows construction of a forced expression system of manR of a koji mold using a TEF1 promoter.

For the purpose of enhancing the expression of the mannan hydrolases of a koji mold, a koji mold forcibly expressing manR was produced. FIG. 14 shows the outline of the forced expression system. A marker gene, ptrG, and a TEF1 promoter were inserted between the promoter portion of manR and the structural gene of manR so that manR is under the control of the TEF1 promoter and is constitutively expressed. The strain forcibly expressing manR was produced as follows. First, a vector was produced by fusion PCR. The sequences of oligonucleotide primers used in this PCR are shown in Table 10.

TABLE 10

| No. | Sequence |
|---|---|
| SEQ ID NO: 37 | TGAGTTAAGCGCCATGAGGGAGTATGTC |
| SEQ ID NO: 38 | GTACGTCTGTTGTACGCCAGGTGAGGAGTTTACGAGGATAC |
| SEQ ID NO: 39 | TAAACTCCTCACCTGGCGTACAACAGACGTACCCTGTGATGTTC |

TABLE 10-continued

| No. | Sequence |
|---|---|
| SEQ ID NO: 40 | TGTTGACAGACTACGGATAAACTGCACCTCAGAAGAAAAGGATG |
| SEQ ID NO: 41 | CTGAGGTGCAGTTTATCCGTAGTCTGTCAACATTGCCTCTTTG |
| SEQ ID NO: 42 | AATCGATCAGAACCGGCCAACACAACTCGACGGGTTGATAAACTTAC |
| SEQ ID NO: 43 | CGTCGAGTTGTGTTGGCCGGTTCTGATCGATTTGGATCTAAG |
| SEQ ID NO: 44 | ATCCATACCGTGCCCTTTCCTAAAAGAC |

The underlines in the sequences show added sequences that are used in fusion PCR, and the sequences are regions that do not anneal to the template DNA in the first-stage PCR.

First, DNA fragments of the right and left arms (fragments R and L) for homologous recombination, the TEF1 promoter, and pyrG (fragment P) serving as a marker gene for transformation were amplified by a PCR method.

In the PCR, KOD plus (manufactured by TOYOBO), which has high accuracy, was used as in above. The final concentration of MgSO4 in the reaction solution was adjusted to 1.2 mM in amplification of fragments L and R and the TEF 1 promoter and was adjusted to 2.0 mM in amplification of fragment P. Dimethyl sulfoxide (manufactured by Sigma-Aldrich Japan) was optionally added to the reaction solution at a final concentration of 5.0 to 7.0%.

As the primers for the PCR, a set of those represented by SEQ ID NOs: 37 and 38 was used in amplification of fragment L; a set of those represented by SEQ ID NOs: 43 and 44 was used in amplification of fragment R; a set of those represented by SEQ ID NOs: 41 and 42 was used in amplification of the TEF1 promoter; and a set of those represented by SEQ ID NOs: 39 and 40 was used in amplification of fragment P. As the template for the PCR reaction, 150 ng of genomic DNA of the wild-type strain was used, and the reaction system was adjusted to a total amount of 50 µL. The PCR reaction was performed at 94° C. for 2 min and then 30 cycles of 94° C. for 10 sec, 55° C. for 15 sec, and 68° C. for 2 min and 30 sec. A part of the amplification product was subjected to electrophoresis on a 0.8% agarose gel to confirm that DNA fragments of 2.1 kb and 2.8 kb were amplified in fragments L and R; a DNA fragment of 0.9 kb was amplified in the TEF1 promoter; and a DNA fragment of 2.2 kb was amplified in fragment P.

After the confirmation of the amplification by electrophoresis, all of the remaining DNA fragments of fragments L, R, and P were subjected to electrophoresis on a 0.8% agarose gel. The DNA fragments were purified by gel extraction, and 1.1 µL of fragment L, 1.1 µL of fragment R, 3.4 µL of the TEF1 promoter, and 3.4 µL of fragment P were mixed. The resulting mixture was used as a template for fusion PCR.

Then, the four fragments were linked by fusion PCR. In the PCR, KOD plus (manufactured by TOYOBO), which has high accuracy, was used. The final concentration of MgSO4 in the reaction solution was adjusted to 1.2 mM, and dimethyl sulfoxide (manufactured by Sigma-Aldrich Japan) was added to the reaction solution at a final concentration of 5.0%. As the primers for the PCR, a set of those represented by SEQ ID NOs: 37 and 44 was used. As the template for the PCR reaction, 9 µL of the solution mixture of fragments L, R, TEF1, and P prepared above was used, and the reaction system was adjusted to a total amount of 300 µL. The PCR reaction was performed at 94° C. for 2 min and then 30 cycles of three steps consisting of 94° C. for 10 sec, 58° C. for 15 sec, and 68° C. for 9 min.

A part of the amplification product was subjected to electrophoresis on a 0.7% agarose gel to confirm that DNA fragment of about 7.9 kb was amplified. After the confirmation of the amplification by the PCR reaction, all of the remaining reaction solution was subjected to electrophoresis on a 0.7% agarose gel. The DNA fragment was purified by gel extraction and was then concentrated by alcohol precipitation. Then, the precipitate was used as a vector for forced expression of manR of a koji mold.

This vector was introduced into the above-described host strain by a common method, i.e., a protoplast-PEG method (Gene, 61: 385, 1987).

The selection of transformants was performed by pyrG positive selection using a Czapek-Dox minimal medium containing 1.2 M sorbitol, but not containing uridine. The induction of the resulting transformant into a vector was confirmed by Southern hybridization method and a PCR method.

Figure 15:
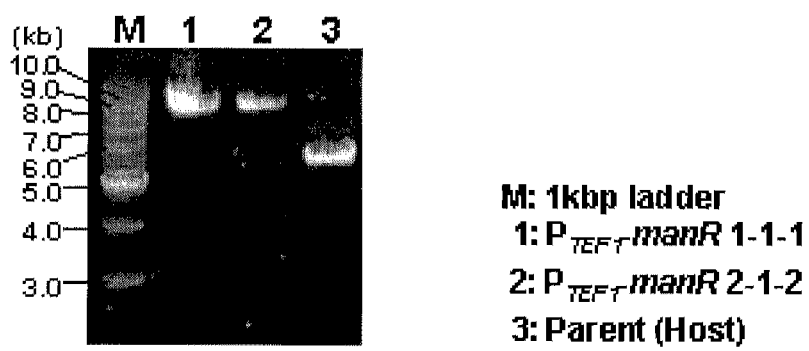
FIG. 15 shows the confirmation results of induction of a vector for manR forced expression system by PCR.

Whether the vector was correctly induced in the produced manR forced expression strain was investigated by a PCR method. First, genomic DNA was prepared by the method described in Example 3 from the forced expression strain and the host strain. PCR was performed using this genomic DNA as a template and a primer set of those represented by SEQ ID NOs: 37 and 44. As the enzyme for PCR, ExTaq (manufactured by Takara Bio) was used. The PCR reaction was performed at 94° C. for 2 min and then 30 cycles of three steps consisting of 94° C. for 10 sec, 58° C. for 15 sec, and 72° C. for 9 min. The results of this PCR are shown in FIG. 15.

A single band of about 7.9 kg was confirmed in the forced expression strain, while a single band of about 5.6 kb was confirmed in the host strain used in the transformation. This suggests that the vector was correctly induced in the resulting transformant and also that the nucleus was purified.

Figure 16:
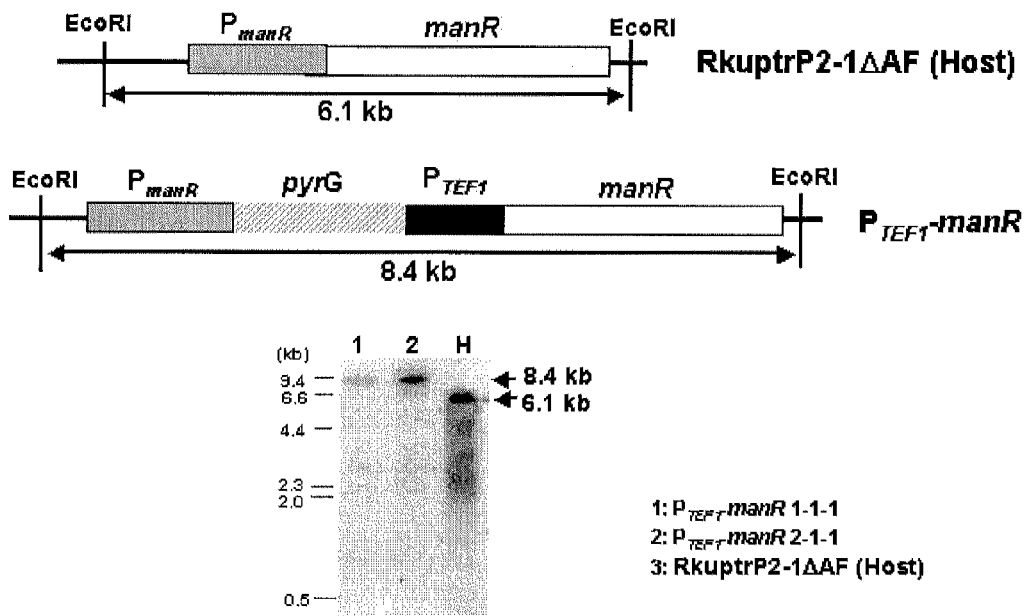
FIG. 16 shows the confirmation results of induction of a vector for manR forced expression system by Southern hybridization.

Whether the vector was correctly induced in the produced strain forcibly expressing manR was investigated by Southern hybridization method. In accordance with the method described in Example 3, the host strain and the manR forced expression strain were subjected to liquid culture, and the genomic DNA was extracted and purified. Each 5.0 µg of the obtained genomic DNA was digested by restriction enzyme EcoRI (manufactured by Nippon Gene) at 37° C. overnight and then subjected to electrophoresis on a 0.8% agarose gel and then blotted onto Hybond-N+ (manufactured by GE Healthcare Biosciences). After the blotting, hybridization was performed at 42° C. overnight using a digoxigenin (DIG)-labeled probe. As the labeled probe, that described in Example 5 was used. The washing of the membrane and the detection of signals after the hybridization were performed in accordance with the manual of a DIG system (manufactured by Roche Diagnostics). The results are shown in FIG. 16.

In each of the manR forcibly expressing strain and the host strain, a single band was detected. In the disruptant, the band was observed at about 8.1 kb while the band of the host strain was observed at about 6.1 kb. Thus, an obvious difference between the both was confirmed. The sizes of these bands agreed with the theoretical values. It was judged from the results that the vector for manR forced expression was correctly introduced and that the nucleus of the strain was purified. Incidentally, this manR forced expression strain (Aspergillus oryzae PTEF 1 manR, 2-1-2) has been deposited (Accession No. FERM BP-11104) in International Patent Organism Depositary, National Institute of Advanced Industrial Science and Technology, Tsukuba Central 6, 1-1-1 Higashi, Tsukuba, Ibaraki, Japan on Mar. 3, 2009, under the provisions of "the Budapest Treaty on the International Recognition of the Deposit of Microorganism for the Purposes of Patent Procedure".

Example 19

Halo Assay of manR Forced Expression Strain Using Glucomannan Plate

Figure 17:
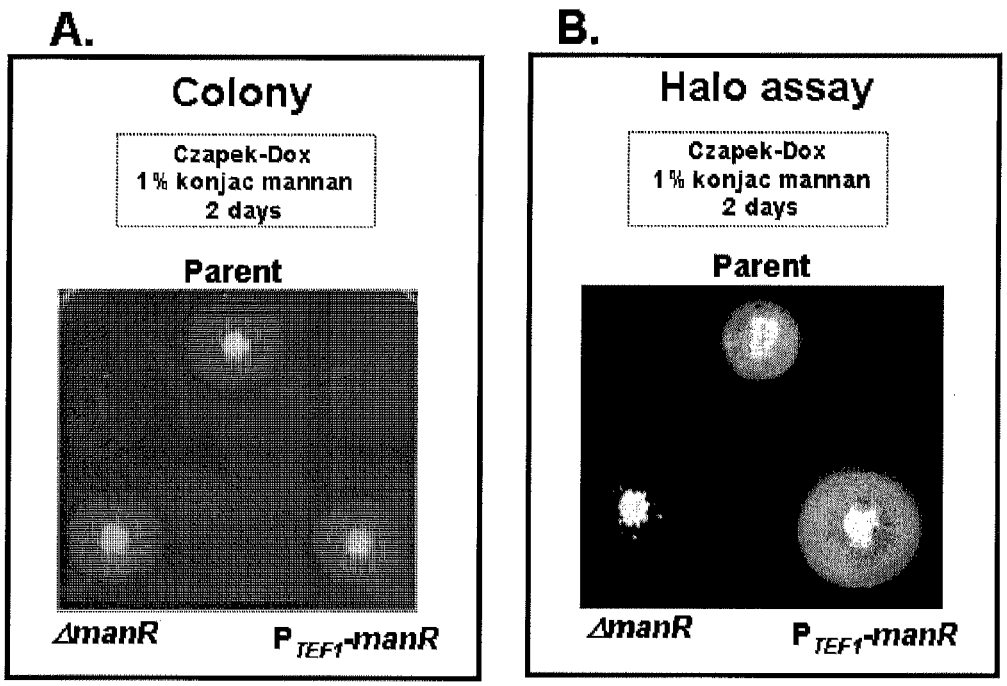
FIG. 17 shows the results of a halo assay of a koji mold manR forced expression strain and a disruptant.

In order to investigate influence of forced express of manR on mannan hydrolases, a halo assay using a glucomannan plate was performed. 250,000 conidiospores of each of the manR disruptant, the manR forced expression strain, and the control strain were inoculated in each point of a Czapek-Dox minimal medium containing 1.0% glucomannan (manufactured by Megazyme) and were cultured at 30° C. for 2 days. After completion of the culture, halos formed by the extracellular mannanase activity were detected in accordance with the halo assay method of mannanase described in Example 2. The results of the halo assay are shown in FIG. 17.

As shown in FIG. 17A, no significant changes were found in the shapes of colonies of these three strains, but a slight deterioration in the growth of the manR forced expression strain was observed. In the results of the halo assay shown in FIG. 17B, the size of the halo in the manR forced expression strain was significantly large compared with that of the control strain. Thus, an enhancement in production of mannan hydrolases due to forced expression of manR was confirmed. In contrast, in the manR disruptant, halo of mannanase was not found. The growth rates of the three strains subjected to the test did not largely differ from one another. Accordingly, this difference in size of halos is not caused by the difference in growth of the strains, but is probably caused by the difference in amount of mannanase production. From the above, it was confirmed that the amount of mannanase produced by a koji mold varies depending on the expression amount of manR. In addition, the data of this Example supports that manR positively regulates the expression of mannan hydrolases by a koji mold.

Example 20

Enhancement of Production of Mannan Hydrolases by Koji Mold Through Forced Expression on manR In the halo assay using the agar gel described in Example 19, it was confirmed that the forced expression on manR enhances the production of mannan hydrolases by a koji mold. However, it is known that the production amount of glycoside hydrolases such as glucoamylase by a koji mold is larger in the solid culture than that in the culture in an agar medium. Accordingly, whether the forced expression of manR of a koji mold increases the production amount of mannan hydrolases in solid culture using wheat bran was investigated. The method thereof is as follows. 5 g of 80% watering wheat bran was put in a 150-mL Erlenmeyer flask, and the flask was plugged with a cotton plug and was sterilized in an autoclave at 121° C. for 30 min. 10,000,000 conidiospores of each of the manR forced expression strain and the control strain were inoculated to this medium and were cultured at 30° C. The sample was stirred while being loosened after 21 hr from the start of culture and was then further cultured at 30° C. for 43 hr. After completion of the culture, 20 mL of a 50 mM sodium acetate buffer solution (pH 5.0) was added to each sample, and the sample was sufficiently suspended therein. The resulting suspension was filtered through a filter (No. 2, manufactured by ADVANTEC). 1 mL of the resulting filtrate was put in a 1.5-mL plastic microtube, and solid content was removed by centrifugation at 10,000×g for 15 min at 4° C. The resulting sample was used in the following measurement of enzyme activity.

Figure 18:
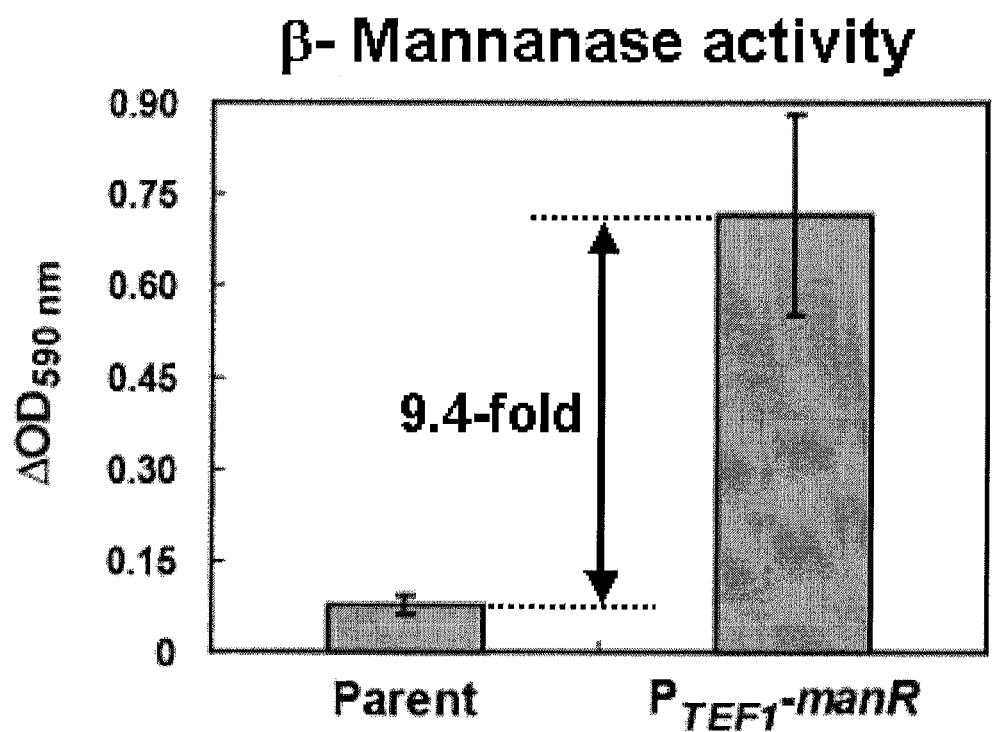
FIG. 18 shows a fluctuation in the amount of produced mannanase during wheat bran culture of a koji mold manR forced expression strain.

First, mannanase activity of the wheat bran extract was measured. To 50 μL of a substrate solution prepared by dissolving 2% (W/V) Azo-Carob-Galactomannan (manufactured by Megazyme) in a 50 mM sodium acetate buffer solution (pH 5.0), 50 μL of the extract was added. The resulting mixture was stirred with a vortex mixer for 5 sec and was allowed to react at 37° C. for 30 min. The reaction was stopped by adding 250 μL of 99.5% ethanol to the reaction solution, and then the solution was left to stand at room temperature for 10 min. Furthermore, this solution was centrifuged at 500×g for 10 min to precipitate unreacted macromolecular substances. The absorbance of the supernatant was measured at 590 nm, which is the absorption maximum of azo dye released by hydrolysis, to quantitatively measure the mannanase activity. Separately, an enzyme solution was treated at 100° C. for 10 min to inactivate the enzyme in advance, and this solution was applied to the same reaction as that of the sample, and the measured value was used as the blank value of each sample. This experiment was conducted in independent triplicates from the culture. The results of the activity measurement are shown in FIG. 18.

The extract from the manR forced expression strain showed high mannanase activity about 9.4-fold that of the extract from the control strain. This revealed that the forced expression of manR of a koji mold very efficiently enhances the production of mannanase even in solid culture using wheat bran.

Figure 19:
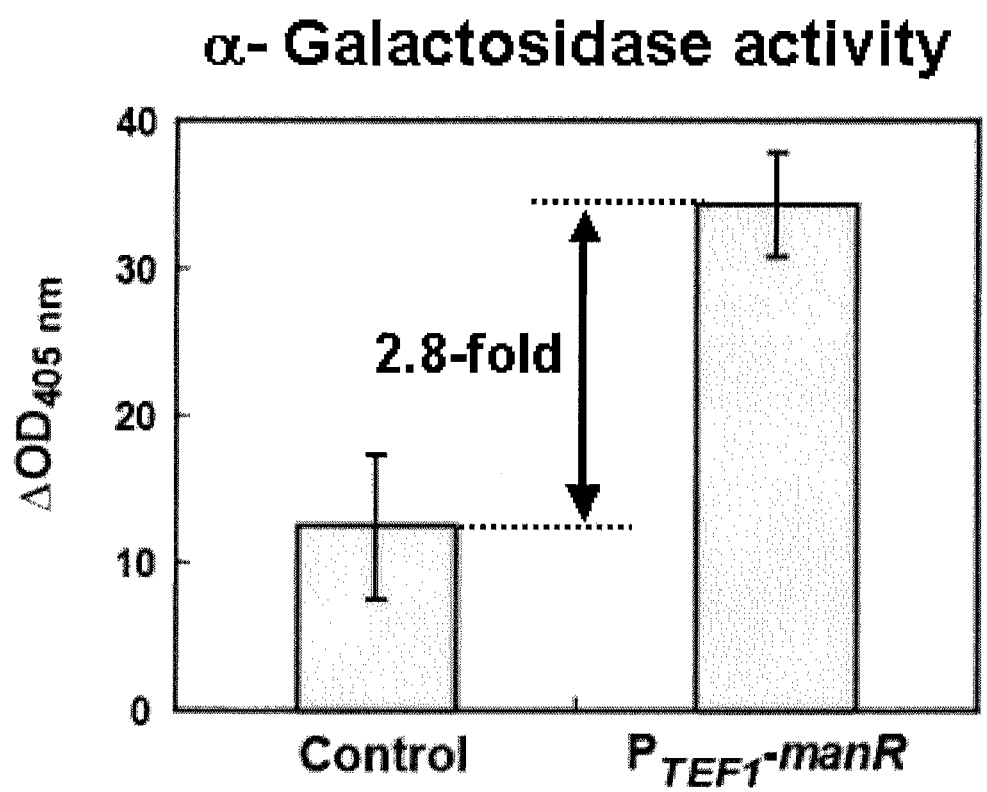
FIG. 19 shows a fluctuation in the amount of produced α-galactosidase during wheat bran culture of a koji mold manR forced expression strain.

Next, α-galactosidase activity of the wheat bran extract was measured. First, each extract was diluted 100 fold with a 50 mM sodium acetate buffer solution (pH 5.0). To 20 μL of each diluted extract, 40 μL of a 50 mM sodium acetate buffer solution (pH 5.0) and 40 μL of 2.5 mM p-nitrophenyl-α-D-galactopyranoside (manufactured by Wako Pure Chemical Industries) were added, followed by a reaction at 37° C. for 15 min. The reaction was stopped by adding 100 μL of a 500 mM sodium carbonate solution to the reaction solution. The absorbance was measured at 405 nm, which is the absorption maximum of p-nitrophenol released by hydrolysis, to quantitatively measure the α-galactosidase activity. As a blank, a 50 mM sodium acetate buffer solution (pH 5.0) was used instead of the sample, and the amount of autolysis of the substrate was measured. After the measurement, the enzyme activity of the undiluted extract was calculated by multiplying the value (ΔOD405 nm) obtained by subtracting the blank value from the measured value by 100, which is the dilution rate. This experiment was conducted in independent triplicates from the culture. The results of the activity measurement are shown in FIG. 19.

The extract from the manR forced expression strain showed high α-galactosidase activity about 2.8-fold that of the extract from the control strain. This revealed that the forced expression of manR of a koji mold enhances the production of α-galactosidase, which is necessary for degradation of side chains of galactomannan as well as mannanase, even in solid culture using wheat bran.

The results shown in Example 20 prove that forced expression of a transcription regulatory factor, "manR", of a koji mold can efficiently enhance the expression of mannan hydrolase under solid culture conditions, which are widely used in production of enzymes for industrial purposes.

Example 21

Halo Assay of Extracellular Cellulase Activity in manR Forced Expression Strain and Disruptant If the transcription regulatory factor positively regulates the gene expression of cellulose hydrolases, as well as mannan hydrolases, it can be expected to breed a koji mold that can over-produce both the hydrolases by forced expression of the transcription regulatory factor. Accordingly, forced expression and disruption of manR were applied to the cellulase halo assay described below to investigate whether a change in expression amount of manR affect the production amount of cellulase by the koji mold. A sample to be tested was inoculated to a plate of a Czapek-Dox minimal medium (0.05% KCl, 0.2% NaNO3, 0.1% KH2PO4, 0.05% MgSO4, 0.001% FeSO4, and 2.0% agar) containing 2.0% carboxymethyl cellulose (manufactured by Sigma-Aldrich) as a single carbon source and was cultured at 30° C. for 3 days. After completion of the culture, about 8 mL of 0.25% Congo red was added to the plate for staining added for 15 min, followed by washing the plate with about 8 mL of a 1.0 M NaCl solution for 30 min three times. After completion of the washing, about 3 to 5 mL of 5.0% (V/V) acetic acid was added to the plate, and the plate was left at room temperature for about 10 min to change the color of the Congo red to blue to detect halo formed by the extracellular cellulase activity. In this experiment, the control strain was used as a positive control. The results are shown in FIG. 20.

In the manR forced expression strain, the cellulase activity was significantly increased compared with that in the control strain. In contrast, in the disruptant, the size of the halo was significantly small, compared with that in the control strain. It is obvious from this that manR regulates not only the production of extracellular mannanase but also the production of extracellular cellulase in the koji mold and that forced expression of manR can enhance the ability of the koji mold to produce extracellular cellulase.

Example 22

Identification of Cellulose Hydrolase Under manR Regulation by DNA Microarray Analysis of manR Forced Expression Strain and Disruptant In order to identify a cellulose hydrolase gene under regulation of manR, DNA microarray analysis of a manR disruptant was performed. The method is as follows. About 10,000,000 conidiospores of each of the manR forced expression strain, the disruptant, and the control strain were cultured in 40 mL of a Czapek-Dox minimal medium in a 150-mL Erlenmeyer flask for 18 hr to germinate. After completion of the culture, the cells were collected by sterilized Mira-Cloth (manufactured by Calbiochem). The collected cells were cultured in a Czapek-Dox minimal medium containing 2.0% Avicel (microcrystalline cellulose, manufactured by Sigma-Aldrich) as a single carbon source at 30° C. for 6 hr at 150 rpm, and then the cells were collected by filtration through sterilized Mira-cloth, dried by absorbing moisture by a paper towel, and were then frozen rapidly using liquid nitrogen. Total RNA was extracted from the cells by the method described in Example 7, and the quantity and the quality of the obtained total RNA were tested. DNA microarray analysis was performed using 500 ng of the total RNA of each sample in accordance with the method described in Example 7. From the results of the DNA microarray experiment, genes of which expression amounts in the dispersant were decreased to 1/10 or less were selected and are shown in FIG. 21.

In the selected genes, a plurality of cellulose hydrolases were confirmed, for example, cellobiohydrolases such as cellobiohydrolase D (GH family 7, AO090012000941), cellobiohydrolase A (GH family 6, AO090038000439), and cellobiohydrolase C (GH family 7, AO090001000348); β-glucanases such as endoglucanase (GH family 5, AO090005001553) and endo-1,3(4)-β-glucanase (GH family 16, AO090113000105); and β-glucosidase (bgl3, AO090003000497, GH family 1), which degrades oligosaccharides generated by the action of cellobiohydrolase or glucanase. The expression of the genes of the above-mentioned six cellulose hydrolases were notably enhanced by forced expression of manR to about 8.7- to 33-fold that of the control. In addition, regarding mannan hydrolases (e.g., endo-β-mannanase, α-galactosidase, and β-mannosidase) which showed, in Example 7, notable changes in the DNA microarray analysis using konjak mannan as a carbon source, the expression of the genes was notably decreased in the manR disruptant, whereas the expression was obviously enhanced in the forced expression strain. These results suggest that manR can regulate cellulose hydrolases as well as the genes of mannan hydrolases. In addition, in this experiment, though mannans were not contained in the carbon source, genes that are regulated by manR have been successfully identified. This suggests that cello-oligosaccharides such as cellobiose, which are hydrolysis products of cellulose, may be inducers necessary in the manR function.

Example 23

In the enhancement of production of mannan hydrolases in koji molds due to forced expression of manR described in Example 20, the experiment was conducted using "wheat bran" as carbon source containing various types of carbon sources. Whether the expression amount of the genes of cellulose hydrolases are increased by forcibly expressing manR under such conditions was investigated using DNA microarray. The method is as follows. 5 g of 80% watering wheat bran was put in a 150-mL Erlenmeyer flask, and the flask was plugged with a cotton plug and was sterilized in an autoclave at 121° C. for 30 min. 10,000,000 conidiospores of each of the manR forced expression strain, the disruptant, and the control strain were inoculated to this medium and were cultured at 30° C. The sample was stirred for loosening after 21 hr from the start of culture and was then further cultured at 30° C. for 27 hr. After completion of the culture, each culture product was rapidly frozen with liquid nitrogen, and extraction of total RNA and quantitative and qualitative determination of the total RNA were performed in accordance with the method described in Example 7. DNA microarray analysis in accordance with the method described in Example 7 was performed using 500 ng of the total RNA of each sample. From the results of the DNA microarray experiment, genes of which expression amounts in the dispersant were decreased to ⅛ or less were selected and are shown in FIG. 22.

The selected genes included cellobiohydrolase D (GH family 7, AO090012000941) and cellobiohydrolase C (GH family 7, AO090001000348), which showed manR-dependent expression in the experiment (Example 22) using Avicel as a single carbon source, and endoglucanase (GH family 5, AO090005001553). However, genes such as cellobiohydrolase A (GH family 6, AO090038000439), endo-1,3(4)-β-glucanase (GH family 16, AO090113000105), and β-glucosidase (bgl3, AO090003000497, GH family 1), which showed manR-dependent expression in the experiment using Avicel as a single carbon source were not observed, and, instead, another cellulose hydrolases such as end-1,4-β-glucanase, CelB (GH family 7, AO090010000314), endoglucanase (GH Family 12, AO090003000905), endoglucanase (GH Family 61, AO090023000787), and endoglucanase (GH Family 6, AO090038000439) were observed. In the cellulose hydrolases selected in this experiment, only the endoglucanase (GH Family 61, AO090023000787) was not affected by the forced expression of manR, but expression of other cellulose hydrolases was increased in the manR forced expression strain, compared with that of control. Furthermore, as in Example 22, expression of many mannan hydrolases, such as endo-β-mannanase, α-galactosidase, and β-mannosidase, was notably decreased in the manR disruptant. In contrast, the expression in the forced expression strain was enhanced. The results described above revealed that the types of the cellulose hydrolases that are influenced by the manR forced expression partially differ between the case using wheat bran as the carbon source and the case using cellulose as the single carbon source, but the manR forced expression contributes to enhancement of expression of mannan hydrolases and cellulose hydrolases. The reason for the types of cellulose hydrolases that are influenced by manR forced expression vary depending on the culture conditions are probably that some of cellulose hydrolases are simultaneously regulated by not only manR but also another transcription regulatory factor.

Example 24

Figure 23:
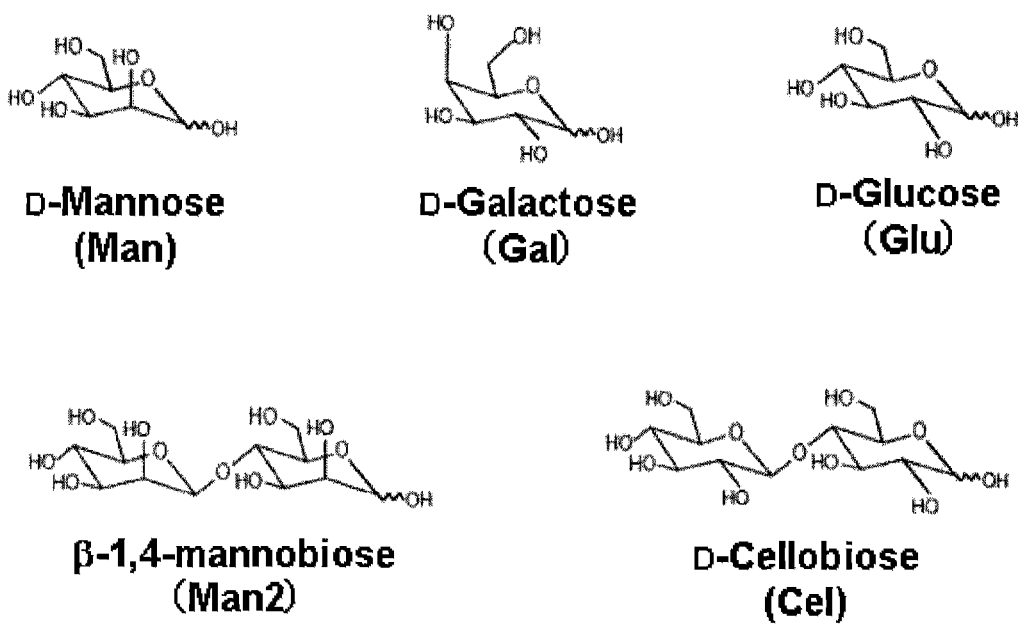
FIG. 23 shows kinds and structures of saccharides used in an addition test.

Search of Inducer of Mannanase and Participation of manR in Inducer-Dependent Expression of Mannanase It has been reported that induction of an enzyme degrading polysaccharides through a transcription regulatory factor derived from a mold needs any inducer in addition to the transcription regulatory factor. For example, it has been reported that in AmyR, a transcription regulatory factor of amylase, isomaltose is an inducer thereof (Curr Genet, 42: 43-50, 2002). In addition, it has been reported that in XlnR, which is a transcription regulatory factor of xylan hydrolases and cellulose hydrolases, D-xylose and D-cellobiose are inducers thereof (J. Gen. Appl. Microbiol., 47, 1-19, 2001). As described above, in some transcription regulatory factors of glycolytic enzymes of molds, enzyme products of which degradation is regulated by such transcription regulatory factors function as the inducers. Accordingly, regarding the induction of endo-β-mannanase through ManR, whether a similar inducer is present or not was investigated. In this experiment, D-mannose, D-glucose, D-cellobiose, and D-galactose (manufactured by Wako Pure Chemical Industries), which are probably generated by degradation of glucomannan and galactomannan, or 1,4-β-D-mannobiose (manufactured by Megazyme) were used. FIG. 23 shows the structures of these saccharides.

Fluctuation in expression of endo-β-mannanase gene by addition of saccharides was measured by quantitative RT-PCR. The method is as follows. About 10,000,000 conidiospores of each of the control strain and the manR forced expression strain were inoculated to 60 mL of a Czapek-Dox medium containing 3.0% citric acid as the carbon source and 0.2% peptone and were cultured at 30° C. for 18 hr at 150 rpm to germinate. The cells were collected by sterilized. Mira-Cloth, and the collected cells were washed with a Czapek-Dox medium containing 1.0% citric acid as a single carbon source. The cells were transferred to 20 mL of a Czapek-Dox medium containing 1.0% citric acid as a single carbon source in a 150-mL Erlenmeyer flask, and filter sterilized monosaccharide and oligosaccharide were added thereto at a final concentration of 0.5 mM. Each sample containing the saccharides was cultured at 30° C. for 2 hr at 150 rpm, and then the cells were collected by filtration. From the cells, RNA was purified and confirmed in accordance with the method described above, and then the expression amount of the mannanase gene (AO090010000122) was measured by a quantitative RT-PCR method. As the quantitative RT-PCR method, an intercalater method using Syber Green I was employed; Brilliant II SYBR Green QRT-PCR Master Mix, 1-Step (Stratagene) was used as the reagent; and MX3000P (Stratagene) was used as the apparatus. The reaction of the quantitative RT-PCR was performed in accordance with the manual of the manufacturer, and 100 ng of total RNA was added to 25 μL, of a reaction system for measurement. The primer concentrations were each 50 pmol, and a HIstone H2B gene (AO090020000006) was used as an internal standard. Data analysis was performed by a Comparative CT method (ΔΔCT method), and MxPro version 3.2 (Stratagene) was used as the software. The sequences of the oligonucleotide primers used in this quantitative RT-PCR are shown in Table 11.

TABLE 11

| No. | Sequence (target gene) |
|---|---|
| SEQ ID NO: 46 | TGCCATCTCAGGGGACCTCTACTG (endo-β-mannanase A) |
| SEQ ID NO: 47 | CCGCAATATGGTCAGTCACGAGAC (endo-β-mannanase A) |
| SEQ ID NO: 48 | ACTCCTTTGTCAATGACATCTTCGAG (histone $H_2$ B) |
| SEQ ID NO: 49 | ATTCACCTGGCAGGATAAGTCTGAC (histone $H_2$ B) |

Figure 24:
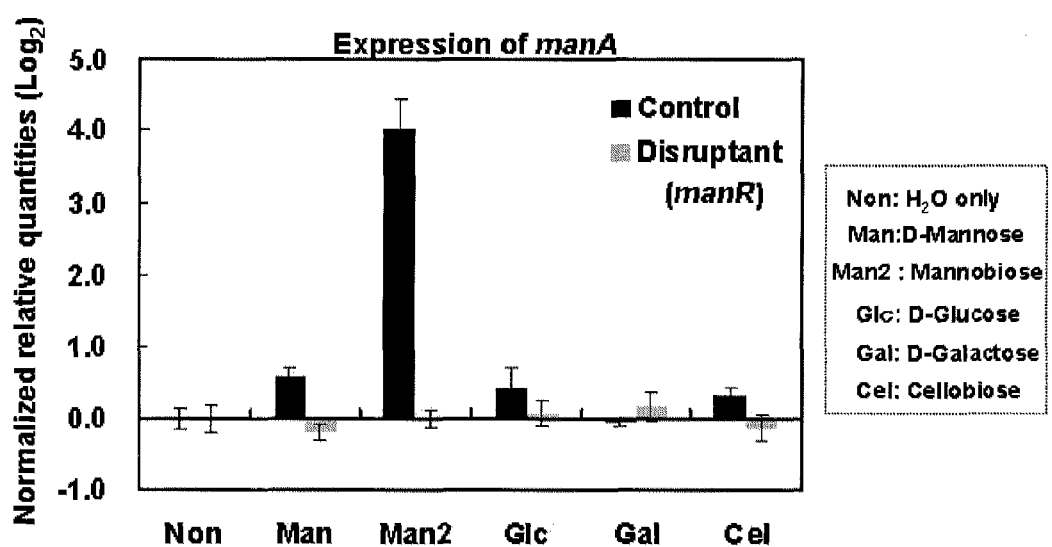
FIG. 24 shows search of mannanase inducers and participation of manR in induction of mannanase expression through an inducer.

The results of the quantitative RT-PCR are shown in FIG. 24. The expression of mannanase was increased 16-fold or more by addition of β-1,4-D-mannobiose, compared with the case of non-addition of β-1,4-D-mannobiose. This revealed that β-1,4-D-mannobiose is a strong inducer of mannanase. Even in the cases of using mannose, glucose, and cellobiose, the expression of this gene was induced, though the degree of the induction was weak, such as two-fold or less. Thus, it was suggested that these substances are also weak inducers of mannanase. It is rational from the results of Examples 22 and 23 that D-glucose and D-cellobiose are inducers. On the other hand, the addition of D-galactose did not show a fluctuation, compared with a negative control. This suggests that D-galactose does not contribute to induction of mannanase.

Next, a test using the manR disruptant under the same conditions as those of the control was performed to investigate whether ManR is necessary for induction of mannase through an inducer. As a result, in the case of the manR disruptant, the expression pattern was the same as that of the negative control even if β-1,4-D-mannobiose or another saccharide was added, and induction of the enzyme was not observed (FIG. 24). The results described above revealed that the presence of ManR is indispensable for expression induction through an inducer of mold mannanase.

Figure 25:
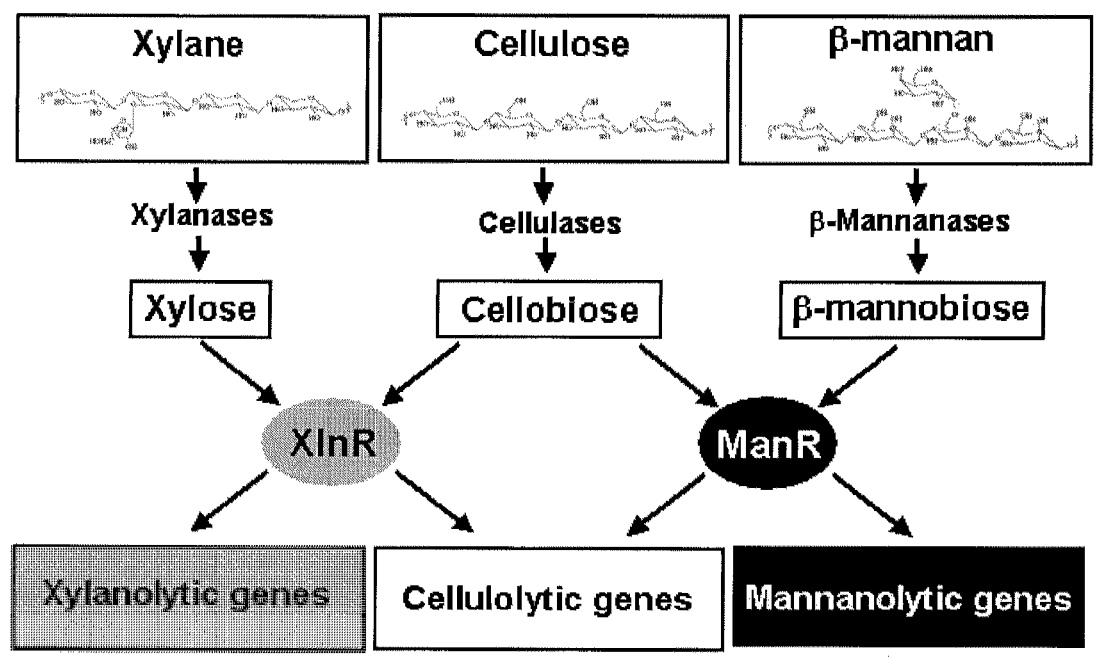
FIG. 25 shows a model of a mechanism for regulating expression of genes of xylane mannan cellulose hydrolases in koji mold.

Regulation of production of cellulose hydrolases and hemicellulose hydrolases through transcription regulatory factor in koji mold FIG. 25 shows the sites on which the transcription regulatory factor (ManR) of the present invention acts in a gene-expression regulatory system of cellulose hydrolases and hemicellulose hydrolases of a koji mold.

Xylane is one of main components of hemicellulose, like β-mannans. It is known that xylanases, which hydrolyze xylane, are regulated in transcription control of XlnR (Fungal Genet Biol, 35: 157-169, 2002). Furthermore, this XlnR is known to regulate the expression of cellulose hydrolases such as cellobiohydrolases and endoglucanases (FEBS Lett, 528: 279-282, 2002). ManR of the present invention does not regulate the expression of the xylanase genes, but regulates mannan hydrolases. In addition, ManR regulates the expression of cellulose hydrolases, like XlnR. In other words, it is suggested that the expression of cellulose hydrolases of a koji mold is regulated by at least two transcription regulatory factors, XlnR and ManR. It is known that the types and contents of hemicelluloses contained in plant cell walls differ between softwood and hardwood (Appl Microbiol Biotechnol, 79, 165-178, 2008). It was supposed that the koji mold distinguish both transcription regulatory factors such that XlnR regulates the xylane degradation system and ManR regulates the β-mannan degradation system, in order to correspond to a variety of compositions of hemicelluloses.

It was confirmed that a transformant transformed with a recombinant vector containing the DNA represented by SEQ ID NO: 1 can enhance the production of mannan hydrolases and cellulose hydrolases. In addition, it was revealed that a protein containing the amino acid sequence of SEQ ID NO: 2 encoded by the base sequence of SEQ ID NO: 1 regulates the transcription of expression of genes of mannan hydrolases and cellulose hydrolases.

The invention claimed is:

1. A cDNA encoding a protein consisting of:
   (a) the amino acid sequence of SEQ ID NO: 2; or
   (b) the amino acid sequence of SEQ ID NO: 2, wherein one to five amino acids are deleted or added and having a positive regulating capability of the transcription of genes for mannan hydrolases or cellulose hydrolases.

2. A recombinant vector comprising the cDNA of claim 1.

3. An isolated transformant comprising the recombinant vector of claim 2.

4. A cDNA consisting of the nucleotide sequence of SEQ ID NO:1.

5. A recombinant vector comprising a cDNA consisting of the nucleotide sequence of SEQ ID NO:1.

6. An isolated transformant comprising the recombinant vector of claim 5.

* * * * *